United States Patent [19]
Ballantyne et al.

[11] Patent Number: 5,867,821
[45] Date of Patent: Feb. 2, 1999

[54] METHOD AND APPARATUS FOR ELECTRONICALLY ACCESSING AND DISTRIBUTING PERSONAL HEALTH CARE INFORMATION AND SERVICES IN HOSPITALS AND HOMES

[75] Inventors: Douglas J. Ballantyne, Nepean; Michael Mulhall, Ottawa, both of Canada

[73] Assignee: Paxton Developments Inc., Ottawa, Canada

[21] Appl. No.: 602,468

[22] Filed: Feb. 16, 1996

Related U.S. Application Data

[63] Continuation-in-part of Ser. No. 241,405, May 11, 1994, abandoned.

[51] Int. Cl.⁶ .................................................... G06F 17/60
[52] U.S. Cl. .................. 705/2; 395/200.33; 395/200.47; 705/3; 707/10; 707/104
[58] Field of Search ........................... 395/200.3, 200.33, 395/200.47, 200.48, 200.49; 705/2, 3, 4; 707/1, 10, 104

[56] References Cited

U.S. PATENT DOCUMENTS

| | | | |
|---|---|---|---|
| 4,835,372 | 5/1989 | Gombrich et al. | 235/375 |
| 4,857,716 | 8/1989 | Gombrich et al. | 235/462 |
| 5,065,315 | 11/1991 | Garcia | 364/413.01 |
| 5,077,666 | 12/1991 | Brimm et al. | 364/413.02 |
| 5,133,079 | 7/1992 | Ballantyne et al. | 358/86 X |
| 5,291,399 | 3/1994 | Chaco | 235/375 X |
| 5,301,105 | 4/1994 | Cummings, Jr. | 364/401 |
| 5,319,543 | 6/1994 | Wilhelm | 364/401 |
| 5,418,945 | 5/1995 | Carter et al. | 707/8 |
| 5,490,088 | 2/1996 | Landis et al. | 395/200.67 |
| 5,588,148 | 12/1996 | Landis et al. | 707/1 |
| 5,592,408 | 1/1997 | Keskin et al. | 365/52 |
| 5,699,038 | 12/1997 | Ulrich et al. | 340/286.07 |

*Primary Examiner*—Edward R. Cosimano

[57] ABSTRACT

This new and unique method and apparatus is used for the distribution and administration of medical services, entertainment services, electronic medical records, educational information, etc. to a patient's individual electronic patient care station (PCS) interconnected to a master library (ML) which stores data in digital compressed format, through a local medical information network. The patient/medical personnel interact with this medical information network through the unique PCS and receives the requested service or data from the master library. The data is then displayed either on the associated television set or video monitor or through wireless/IR communications to a peripheral personal data assistant (pen based computer technology) The data for text, audio, and video information is all compressed digitally to facilitate distribution and only decompressed at the final stage before viewing/interaction.

19 Claims, 23 Drawing Sheets

METHOD AND APPARATUS FOR ELECTRONICALLY ACCESSING AND DISTRIBUTING PERSONAL HEALTH CARE INFORMATION AND SERVICES IN HOSPITALS AND HOMES

This is a continuation-in-part application of U.S. patent application Ser. No. 08/241,405 filed May 11, 1994 now abandoned.

BACKGROUND OF THE INVENTION

The present invention relates to a method and apparatus for distribution and administration of medical services, entertainment services, electronic health records, and educational information useful in hospitals, other types of health care facilities, and patients' homes. Presently, some hospitals are automated only to the extent of storing basic patient information, such as patient's name and address, admitting doctor, type of ailment, etc., electronically in computer memory, to be accessed by administrative staff or, at nursing stations, by nurses or other medical personnel. Otherwise, much patient information is collected manually and stored on pages in the patient's file. Of interest to the present invention is our U.S. Pat. No. 5,133,079 entitled an apparatus for the distribution of movies, in which entertainment services, in the form of movies or the like, are delivered electronically in digitally compressed form from a master library to the home or other location of a customer.

Of general background interest to the present invention are the following references, namely Brimm, et al U.S. Pat. No. 5,077,666 (December, 1991) which describes and illustrates the data entry system intended for intensive care, with two display units at each bedside, connected to patient monitoring equipment, which system provides a file server with limited computer functions and some associated disk storage; Cummings, Jr. U.S. Pat. No. 5,301,105 (April, 1994) which teaches a system for health care for patients including a method of payment for billing and a card, personal to a patient, for simple personal identification using magnetic stripe technology; Garcia U.S. Pat. No. 5,065,315 which describes and illustrates a system and method for re-scheduling and reporting patient related services in a hospital, centered on editing procedures and information for a patient and entering information pertinent to a patient's stay in a hospital, including scheduling for tests; Wilhelm U.S. Pat. No. 5,319,543 (June, 1994) directed to a system for central processing of medical records and management of work flow associated with the storing and tracking of electronic medical records based on PC workstations located at nursing stations or physician's offices and Chaco U.S. Pat. No. 5,291,399 (March, 1994) which teaches a system which distributes and processes medical information, optionally by keyboard data entry at a patient's bedside.

OBJECTS OF THE INVENTION

An object of the present invention is to provide a more automated system for distribution and administration of medical services, entertainment services, electronic health records and the like for hospitals, other health care facilities, including the patient's bedside in a hospital or at the patient's domestic premises.

SUMMARY OF THE INVENTION

In accordance with the present invention there is provided an electronic information system for distribution of medical information and patient services which comprises:

(a) a data source in the form of a master library storing data in digital compressed format;
(b) a communications interconnection system electronically associated with the master library;
(c) an automated nursing station electronically associated with the master library through the communications interconnection system for temporary storage of a patient's health records, comprising computer means incorporating a client/server configuration and sufficient memory to temporarily store health records for patients monitored by this station;
(d) an electronic patient care station comprising:
  (i) a monitor screen for display of normal NTSC video, RGB video and other interfaced/non-interlaced digital video formats;
  (ii) interface means to electronically communicate through the communications interconnection system with the master library and with the nursing station;
  (iii) a wireless/IR transmitter/receiver to communicate with a pen based computer device;
  (iv) an input entry device to facilitate the patient/medical staff communication within the system; and
  (v) compression and decompression means for data passed to and from the patient care station.

In a preferred embodiment of the present invention, the system comprises a plurality of nursing stations and one or more patient care stations which are electronically associated with each of the nursing stations. It is preferred that the master library be adapted to store data preferably in digital compressed form selected from one or more of the following:

(a) patient/medical staff health record information,
(b) clinical data including X-Ray, MRI and video images,
(c) patient laboratory data to support medical diagnoses and investigations,
(d) educational/training information in video or textual format for the training of medical personnel and patient requirements,
(e) pharmaceutical databases,
(f) entertainment audio/video data,
(g) monitored video of critical areas including operating rooms and psychiatric wards,
(h) general security video monitoring data, and
(i) management information data including accounting, billing and inventory control/ordering services.

As well, the master library is preferably provided with means to receive and store, in digitally compressed form, data from one or more of the following:

(a) physicians' offices;
(b) clinics and laboratories;
(c) video entertainment libraries;
(d) electronic medical libraries;
(e) hospital security, patient and operating room monitoring information; and
(f) patients' residences.

Through the use of such an electronic information system, many record keeping operations of a typical hospital can be rendered paperless. As well, the collection and distribution of information in the hospital relating to patients, and the delivery of services to patients, as well as many other aspects of hospital administration are significantly facilitated through the use of the system according to the present invention, resulting in enhanced healthcare quality.

BRIEF DESCRIPTION OF THE DRAWINGS

These and other objects and advantages of the invention will become apparent upon reading the following detailed description and upon referring to the drawings in which.

Figure 1:
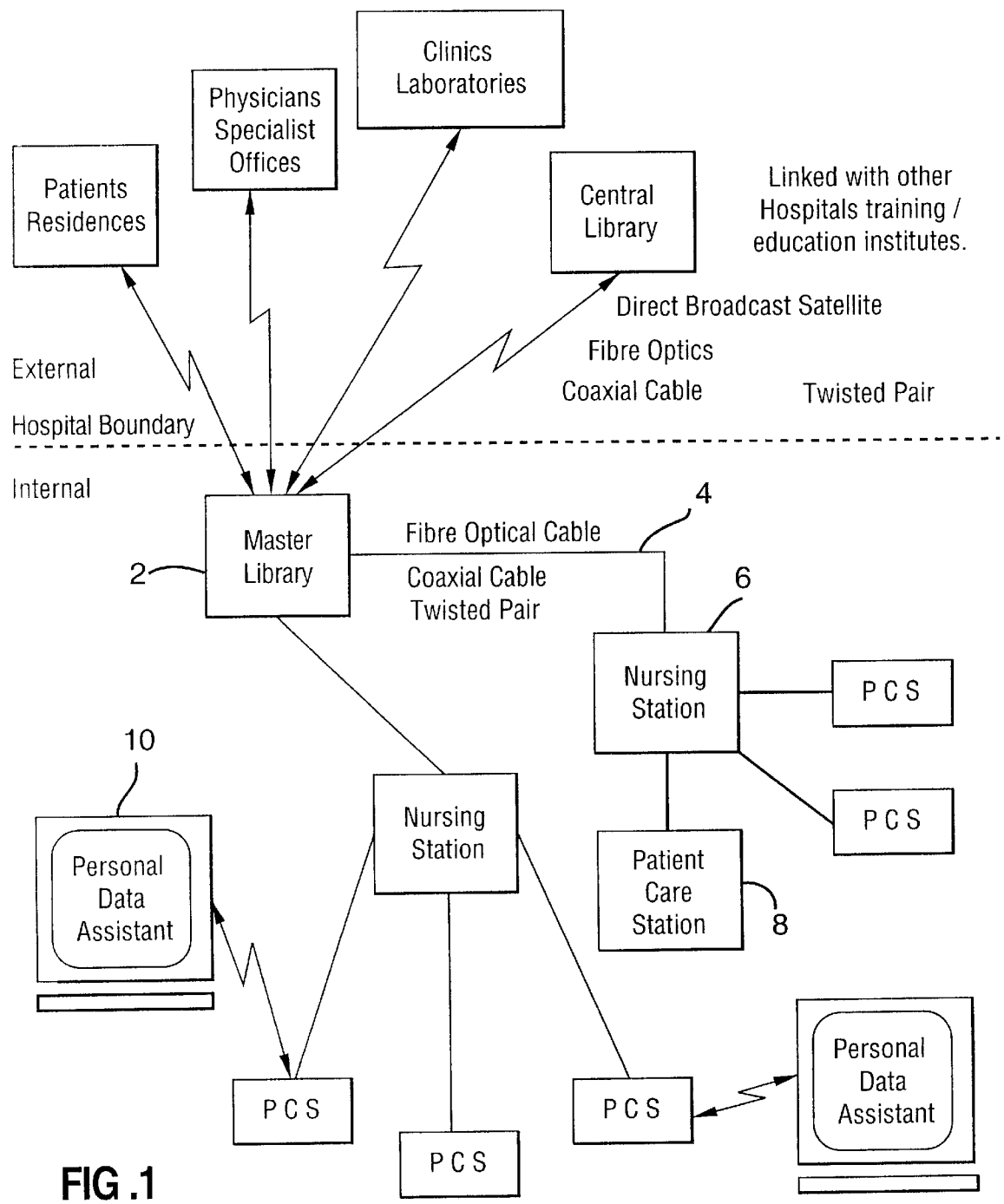
FIG. 1 is a schematic block diagram of a system for distribution of medical information and patient services in a hospital or other such health care institutions, physicians' offices and patients' residences, in accordance with the present invention.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

In the drawings, similar features have been given similar reference numerals.

The medical information network according to the present invention consists of all the related hardware and software components of a master library (ML) (2), a communications interconnection system (4), the distributed processing nursing stations (6), individual bedside patient care stations (PCS) (8), and integrated personal data assistants (PDA) (10). FIG. 1 is a schematic block diagram of the overall system.

The ML, situated locally within the physical boundary of each hospital or by geographical regions serving several hospitals, is configured as a client/server system.

It acts as a medical data depository for all text, audio, and video material including text, graphics, still images, full motion video, and sound/audio information. It includes the storage and processing capabilities to satisfy all administration, medical staff, and patient service requirements. Data is stored in compressed digital format, using typical data compression techniques for text and video image information to minimize memory storage and to facilitate the transmission of data to interconnected user/patient locations. These compression algorithms consist of those listed as follows but are not necessarily limited to those identified:

Text
   Run-length encoding
   Huffman encoding
   Arithmetic coding
   String matching techniques
   LZ-77 and 78 algorithms
Video—MPEG I and II standards
   JPEG standard
   Fractals
   Digital Video Interactive (DVI)
   Audio Video Interleaved (AVI)
   Quicktime
   Vector Quantization (VQ)

The types of data stored in this master library include, but not limited to:

(a) all patient/medical staff health record information, (b) all clinical data including such items as X-Ray, MRI video images, etc.

(c) all patient laboratory data to support medical diagnosis and investigations, (d) educational/training information in video and/or textual format for the training of medical personnel and patient requirements, (e) pharmaceutical databases, (f) entertainment audio/video data, (g) monitored video of critical areas including operating rooms, psychiatric wards, etc., (h) general security video monitoring data, and (i) management information data including account/billing and inventory control/ordering services.

For the distribution of video entertainment information the concept described in Ballantyne, et al U.S. Pat. No. 5,133,079 "Method and Apparatus for the Distribution of Movies" is incorporated in this system.

Figure 2:
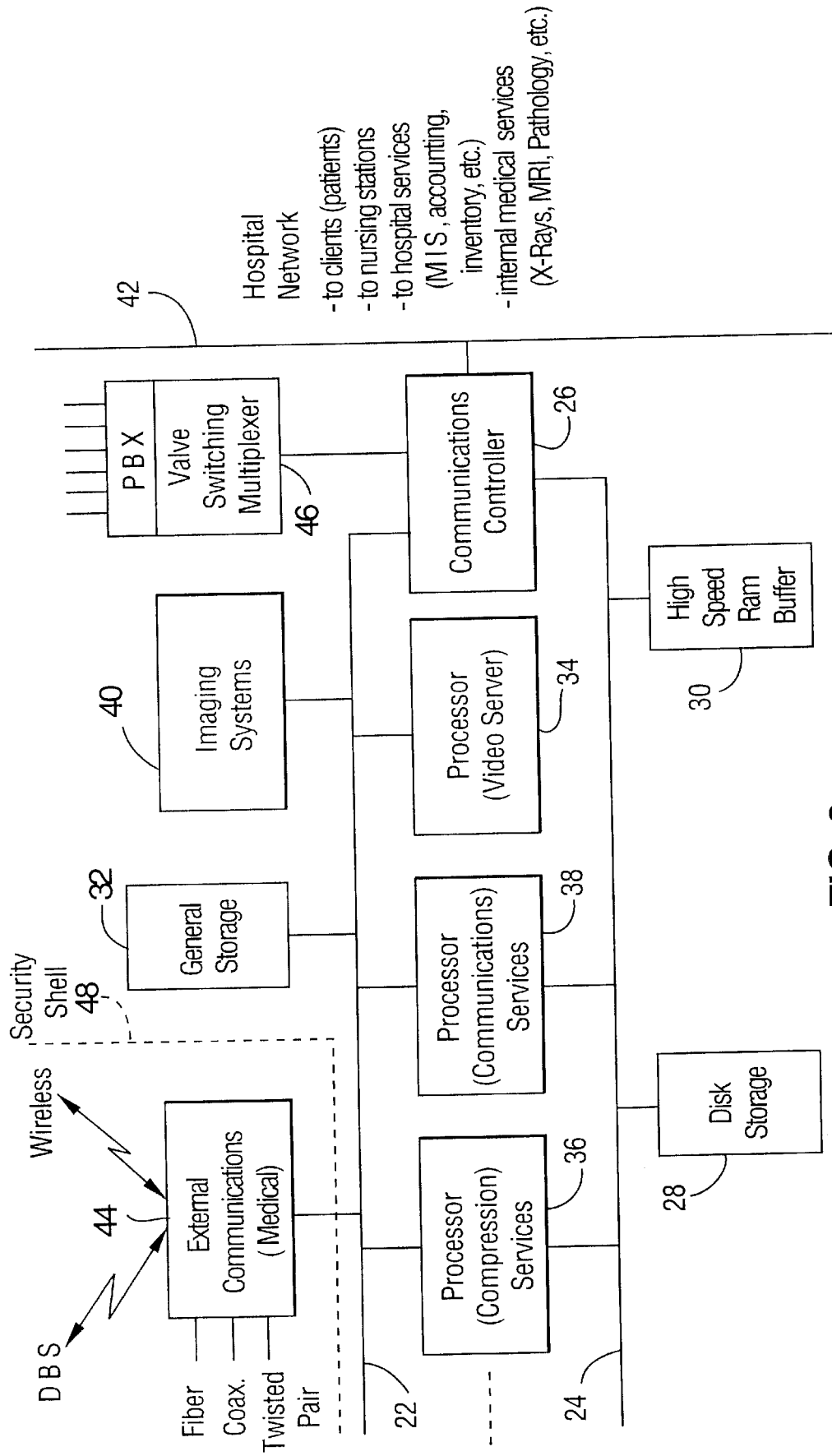
FIG. 2 is a schematic block diagram of an example embodiment of a configuration of the master library of FIG. 1.
Figure 8A:
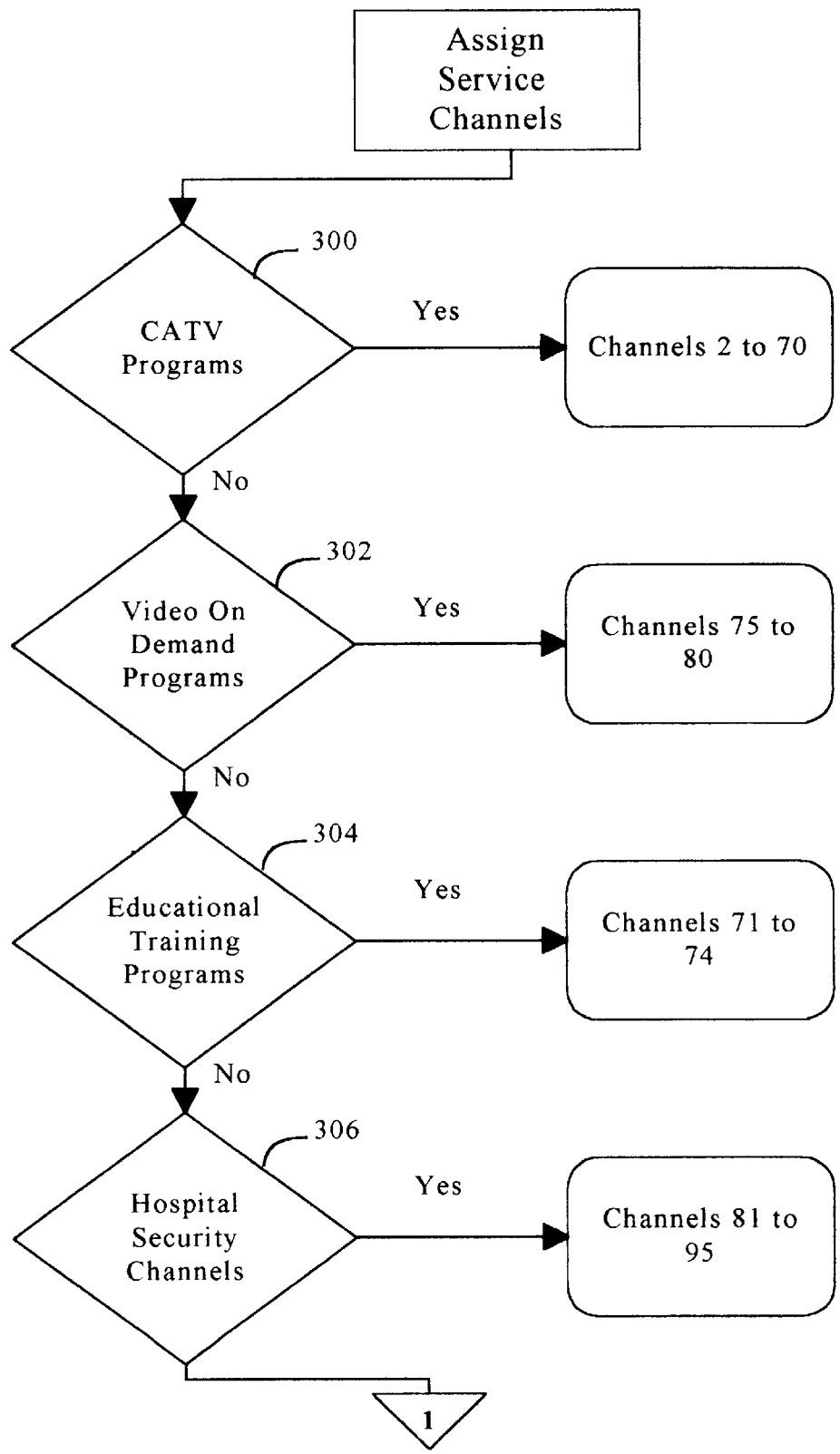
FIGS. 8A and 8B are flow charts describing the process in assigning channels on the internal medical information network to the various services offered to the patients and the medical personnel.
Figure 8B:
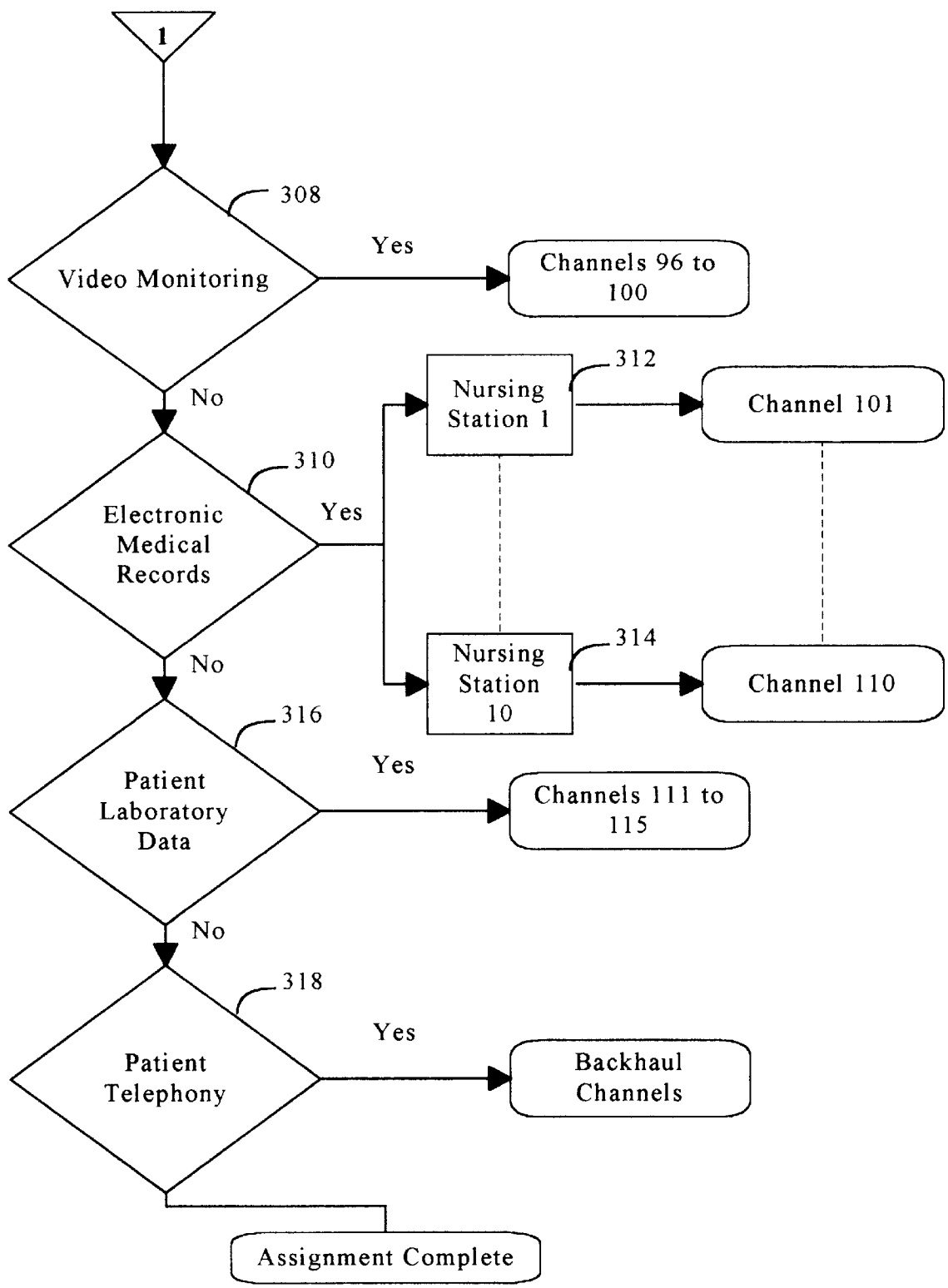

The ML is configured as a client/server computer system to implement the storage and processing of the previously identified items (refer to FIG. 2). The ML consists of various computer servers with each server dedicated to a specific function i.e. a video server (34)for the distribution of video services for patient movie demands, educational/training videos, etc. This video server is based on the technologies available from DEC, Silicon Graphics, N-Cube or ATT/NCR. To facilitate the compression of data, whether text or audio/video data, a compression server system (36) is available. This server system uses compression hardware and software from suppliers such as Optibase, FAST, Xing, etc. to implement data compression to MPEG and JPEG standards. These computer servers are interconnected for administration purposes and general overall data communications via a Local Area Network (22) configured as a fast Ethernet topology and a high speed data bus for the connection to local mass disk storage (28) and RAM memory (30). This high speed bus (24) is based on High-Speed Serial Interface (HSSI), or High-Performance Parallel Interface (HiPPI), or Fiber Distributed Data Interface (FDDI) standards, or other standards that facilitate the rapid distribution of data. These internal networks are interfaced with the Hospital information network through the communications controller (26). This controller is responsible for network channel control, the multiplexing and demultiplexing of data, signal modulation/demodulation, and all data routing between the internal ML network and the Hospital information network. Typical communication controllers conducting these functions are available from vendors such as Scientific Atlanta. Overall communication coordination is effected through the communications server computer (38). Network channels are assigned in accordance with the service being provided, a channel being 6 MHz of bandwidth, equivalent to an analog CATV channel. It is assumed that the internal communications network has a capacity of 750 MHz. of bandwidth (125 channel capacity) whose breakdown is further described in the description of the communications infrastructure. Refer to FIGS. 8A and 8B for the process performed by the communications server in the assignment of the various service channels. These Figures describe the process in assigning channels on the internal medical information network to the various services offered to the patients and the medical personnel. If the service is simple analog cable programming supplied by the local cable companies it is assigned a dedicated channel as it would appear in local TV guides. This ensures a one-to-one correspondence and facilitates patient usage. The first channels (up to channel 70 inclusive) on the network are dedicated to this CATV programming (300). There will be considerable variety in this assignment from geographic region to region but it has been assumed that this first bank of channels is more than adequate to accommodate this variation. The next section of bandwidth (channels 75 to 80) has been allocated to the distribution of Video-On-Demand (VOD) services (302). These VOD services are supplied by the video server existing in the ML. Included in these services are requests for video movies, music videos, and video games. Channels 71 to 74 are used for the distribution of educational and training video material information (304). This material is also maintained in the video server of the ML and can be distributed to all users i.e. broadcast mode or uniquely to individual users. Patients can request training material such as information for new mothers on the correct procedures for the feeding and bathing of newborns or nursing staff can view educational data on new pharmaceuticals and the correct procedures in their administration. The next 15 channels (81 to 95) have been assigned as Hospital security channels (306). More and more video camera security monitoring is being conducted for insurance liability purposes. The video information is compressed at the camera source and stored in a file server at the ML. If more then 15 cameras are to be monitored, time division multiplexing of the data is implemented to accommodate the additional video streams (the Rapid Eye software product from AIT Corporation is to be used to facilitate this security monitoring capability). Specific areas of the hospital, for medical reasons, could require 24 hour video monitoring. This occurs in areas including psychiatric wards where nursing staff observe patients from the nursing stations without actually visiting the patient's premises and also in critical sections such as operating rooms for physician usage and liability issues. The five channels from 96 to 100 are assigned to this dedicated monitoring service (308). The next 10 channels are assigned in order to individual nursing station locations. Each of these channels are dedicated to the distribution of patient electronic medical records (310) with each nursing station temporarily storing the records of the patients that are assigned to the care of that nursing station. The number of nursing station channels (312,314) will vary in accordance with the size of the hospital and thus the number of nursing stations in place. There is sufficient capacity in the network to add extra channels if more nursing stations exist (in the present configuration there are 10 spare channels available). Patient laboratory data (316) is distributed to the nursing stations and the ML over the next 5 channels (from 111 to 115) whereas patient telephony (318) (bedside phone calls) are confined to the back haul channels in the low frequency bandwidth region. Because of the uniqueness of the operations of individual hospitals, the data networking architecture of each hospital will be customized accordingly.

The memory storage media consists of dedicated or combinations thereof of memory devices including optical juke boxes, magnetic memory, magneto or electro-optical memory (28), high speed solid state memory (30), high density tape, etc. to be utilized in accordance with the specific application. Mass memory storage components such as the Ampex DST (32) and Sony's CD-ROM storage systems are typical technologies that satisfy this ML storage requirement. Dedicated text scanning units and imaging systems (40) (Xerox) are integrated with the ML to facilitate the scanning of documents and image material existing in hard copy format.

The ML is interconnected to distributed user sites (i.e. nursing stations and patient bedside units) within the confines of the hospital through an interactive two-way fiber optic cable, coaxial cable, and/or twisted pair cabling (42). The preferred embodiment is a hybrid fiber coax (HFC) configuration. This HFC network provides a downstream (to the patient bedside) frequency bandwidth of 50 to 750 MHz. with an integrated upstream (from the patient's bedside) frequency bandwidth of 5 to 30 MHz. These distributed users can be stand alone dedicated processors (at the bedside) and/or distributed system processors such as those located at the nursing stations. The use of wireless technology is utilized in areas where it is difficult to install suitable cabling or simply areas where wireless communications are more economical.

The ML is linked to external sources via Direct Broadcast Satellite (DBS) equipment, to receive or transmit relevant information. It is also linked to external clinics, other hospitals, medical schools, general practitioner's offices, and patients' residences through landline communications (twisted pair, coaxial cabling, fiber optic cable), DBS or wireless communications (44). A multimedia electronic mail system is implemented amongst authorized users. This facilitates the interaction between external users and the ML i.e. a general practitioner wants to inquire on the latest health care status of one of his/her patients.

The ML is also responsible for implementing voice switched telephony (46), communications between the patient's bedside telephone and the public telephone network. This capability is implemented through the upstream channel available on the HFC network which allows the multiplexing of data, video, and voice over a common integrated fiber/coaxial cable. The technology to facilitate this integration of telephony onto a fiber-coaxial network is available from vendors such as Scientific Atlanta. The appropriate billing and accounting software to monitor patient usage is inherent in this equipment. If the patient telephony communications is implemented via wireless means through equipment such as using Ericsson's Freeset system, the voice switched processor becomes the Freeset's radio exchange connected to an external PBX or Centrex unit.

Figure 3:
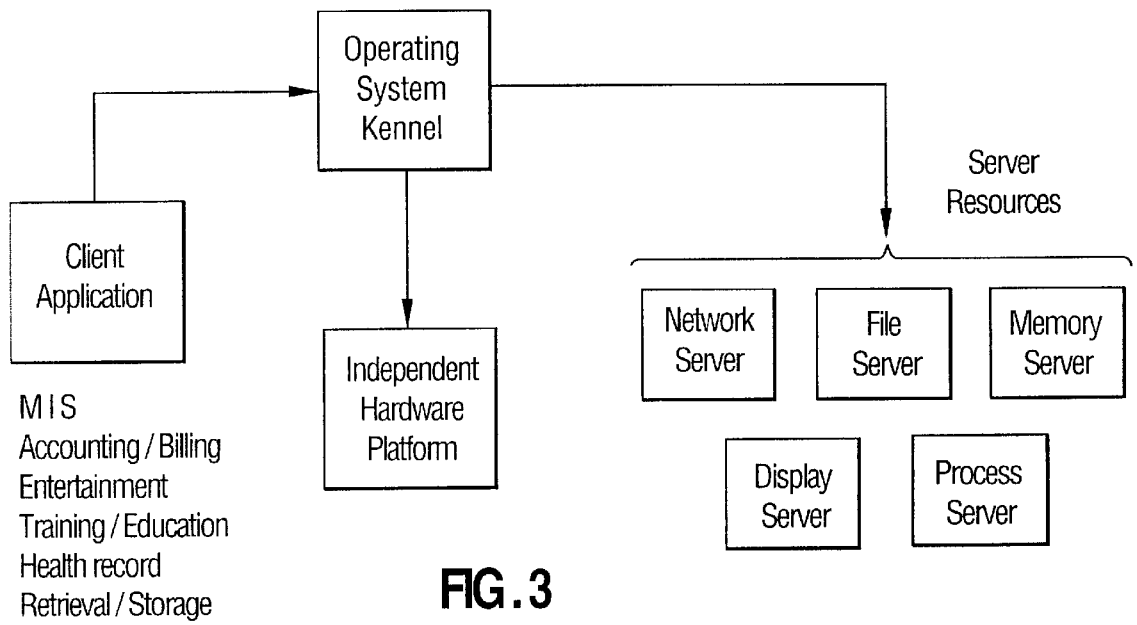
FIG. 3 is a schematic block diagram of an example embodiment of systems software architecture of the system of FIG. 1.

The entire ML and associated medical information network is based on an open client/server computing environment whose systems software architecture is based on Windows NT, or a similar capable Operating System (OS). In this open OS environment the "client" is able to use any vendor application software and the OS provides the appropriate resource "server" to satisfy the user requirement. As a result, it is easy to add or change server functions for they do not depend directly with the selected server hardware. A typical open client/server configuration is depicted in FIG. 3. The overall system applications include management information services, accounting/billing services, inventory control, medical data retrieval, health record retrieval and entry, etc. The system software, residing over an information database, provides a full data storage, search and retrieval capability (as in Fulcrum's SearchTools utility) where every word is a keyword, and thus every word can be searched. This is significantly different from typical keyword searching that only allows specific terms and fields to be set-up as searchable. The following features are inherent in the storage, search and retrieval system:

(1) the system is fully compatible across an array of hardware platforms. This ensures that the distributed nursing stations easily interface, without having to re-process the stored data, with the larger more complex ML.

(2) large data collections normally have complex search requirements which can be wieldy and impractical. In order to facilitate data searches and retrievals of large data collections, the proposed system indexes the data. The index files are then used to support the complex searches, and only those documents that satisfy the search criteria are retrieved.

(3) multiple sources or collections of data can be simultaneously searched. However, identical documents or health records can be maintained in different collections i.e. infants under the age of 5 years, children with digestive disorders that include colic infants—these two data collections would contain similar health records.

(4) comprehensive and thorough search capabilities including logical Boolean searches (AND, OR, and NOT), single words, phrases, multiple words in proximity, etc.

(5) advanced search features such as term weighting (some search terms are more relevant than others), relevance ranking where the search results are ordered in accordance to their importance, intuitive searching where the search is performed on a similarity to a portion of text or document, etc.

(6) maintain and keep search lists to audit previous searches and allow simple modifications to implement a new search query.

(7) support searches on structured and unstructured text, multilingual text, and embedded images.

(8) support searches on native formatted documents such as word processed data i.e. Word Perfect file format.

(9) allow the customization of user interfaces to satisfy unique data entry requirements.

Figure 9A:
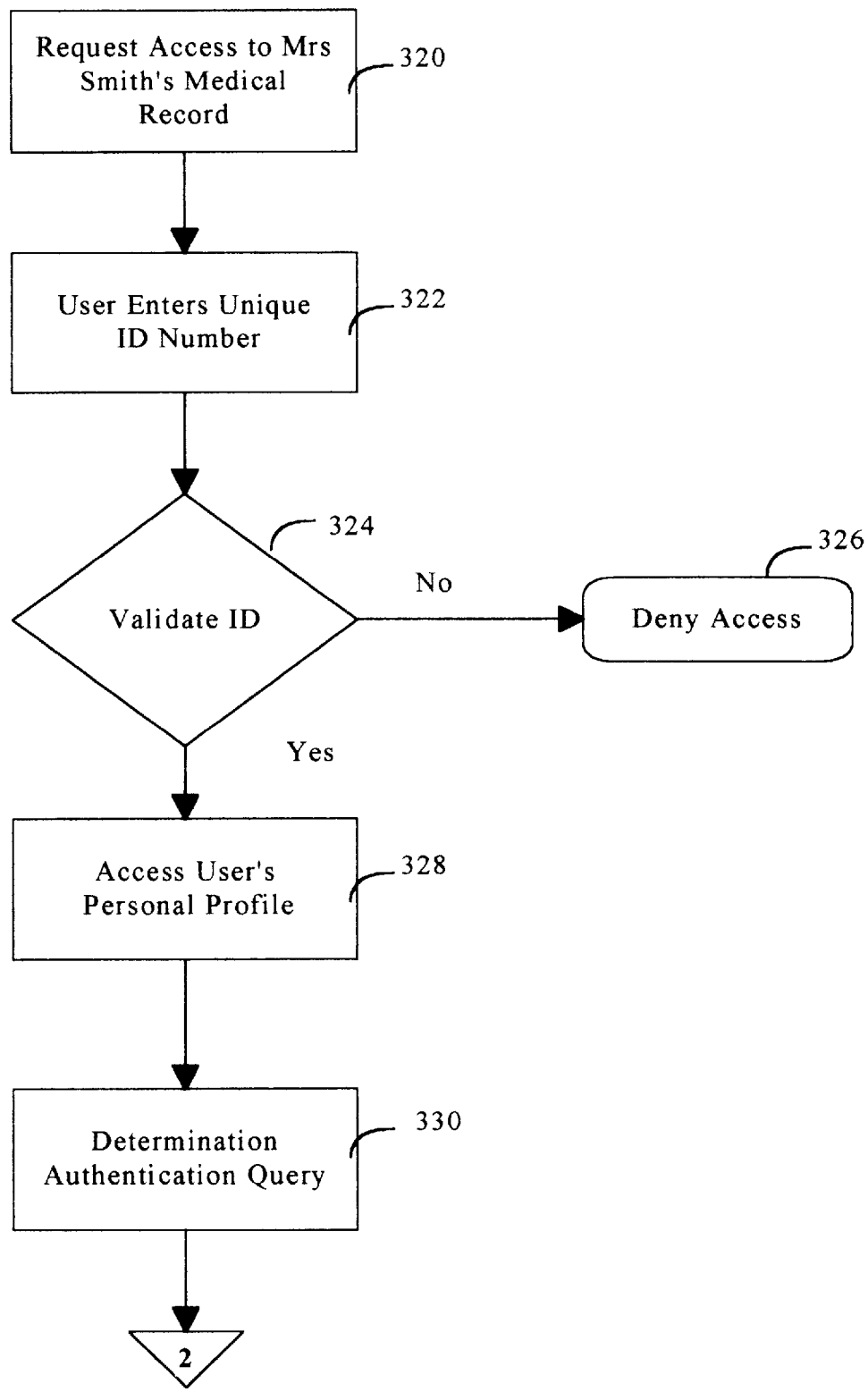
FIGS. 9A, 9B and 9C represent a flow chart depicting the access control and user verification and authentication process that occurs when an individual attempts to gain access to the electronic medical record repository.
Figure 9B:
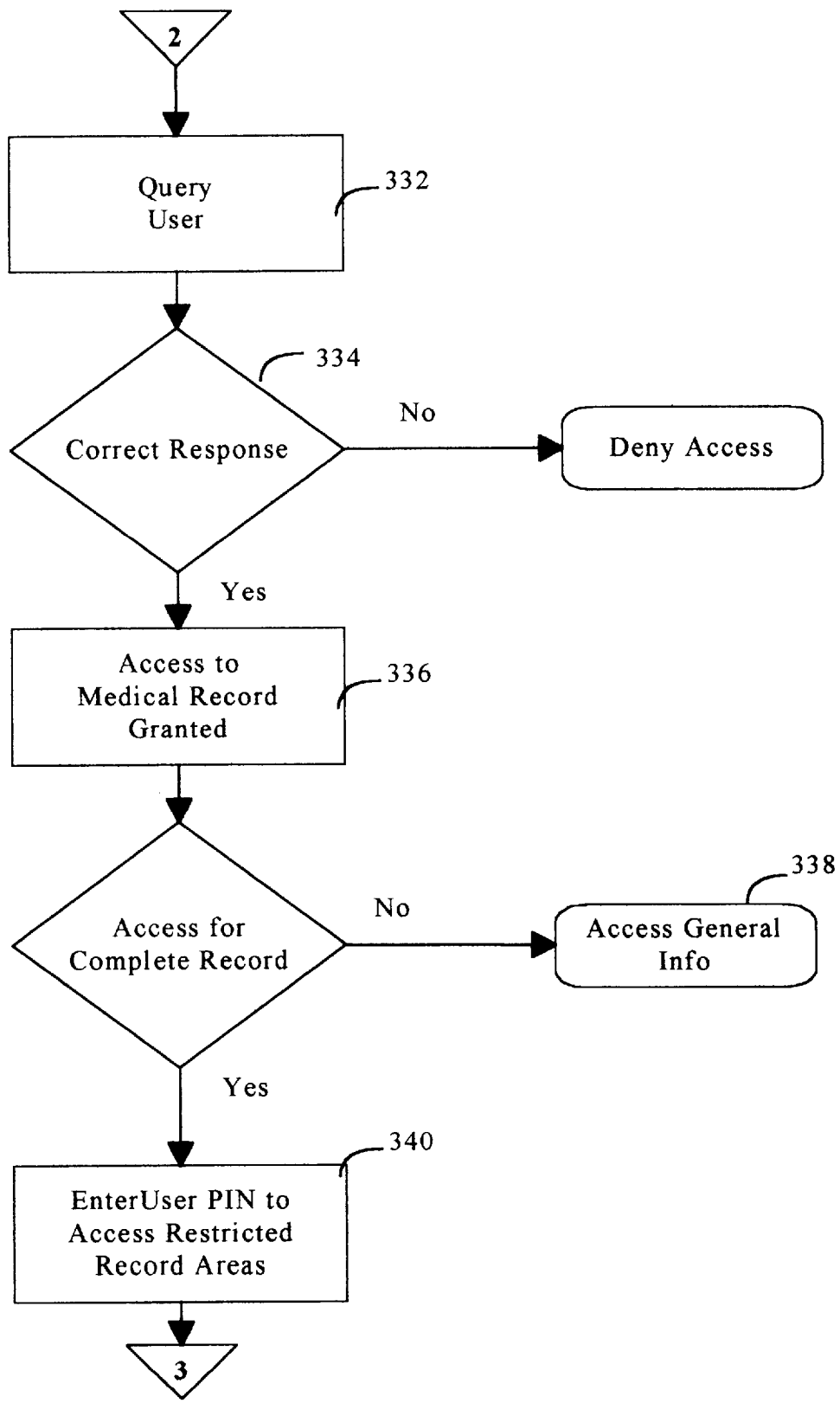
Figure 9C:
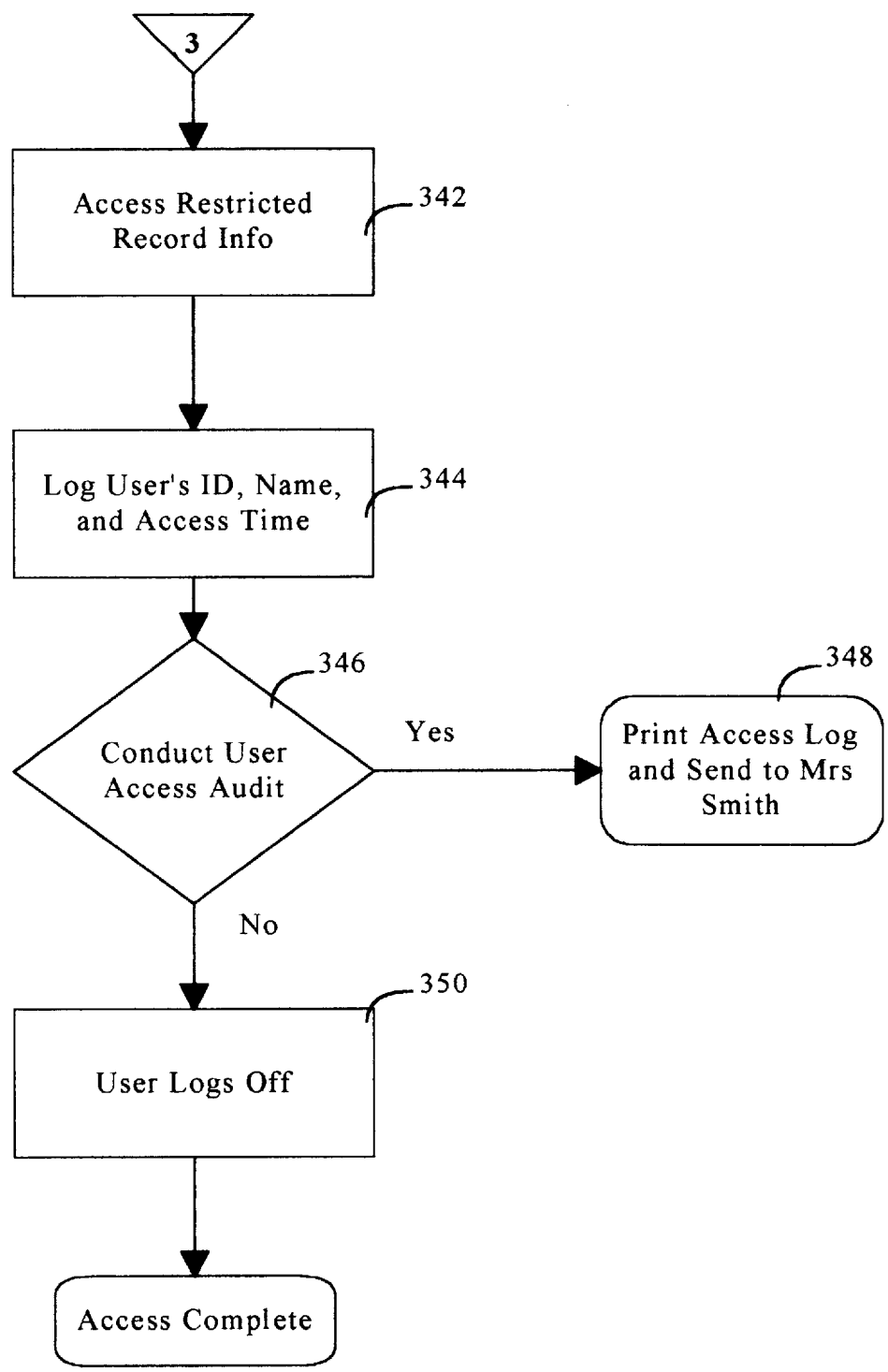
Figure 10A:
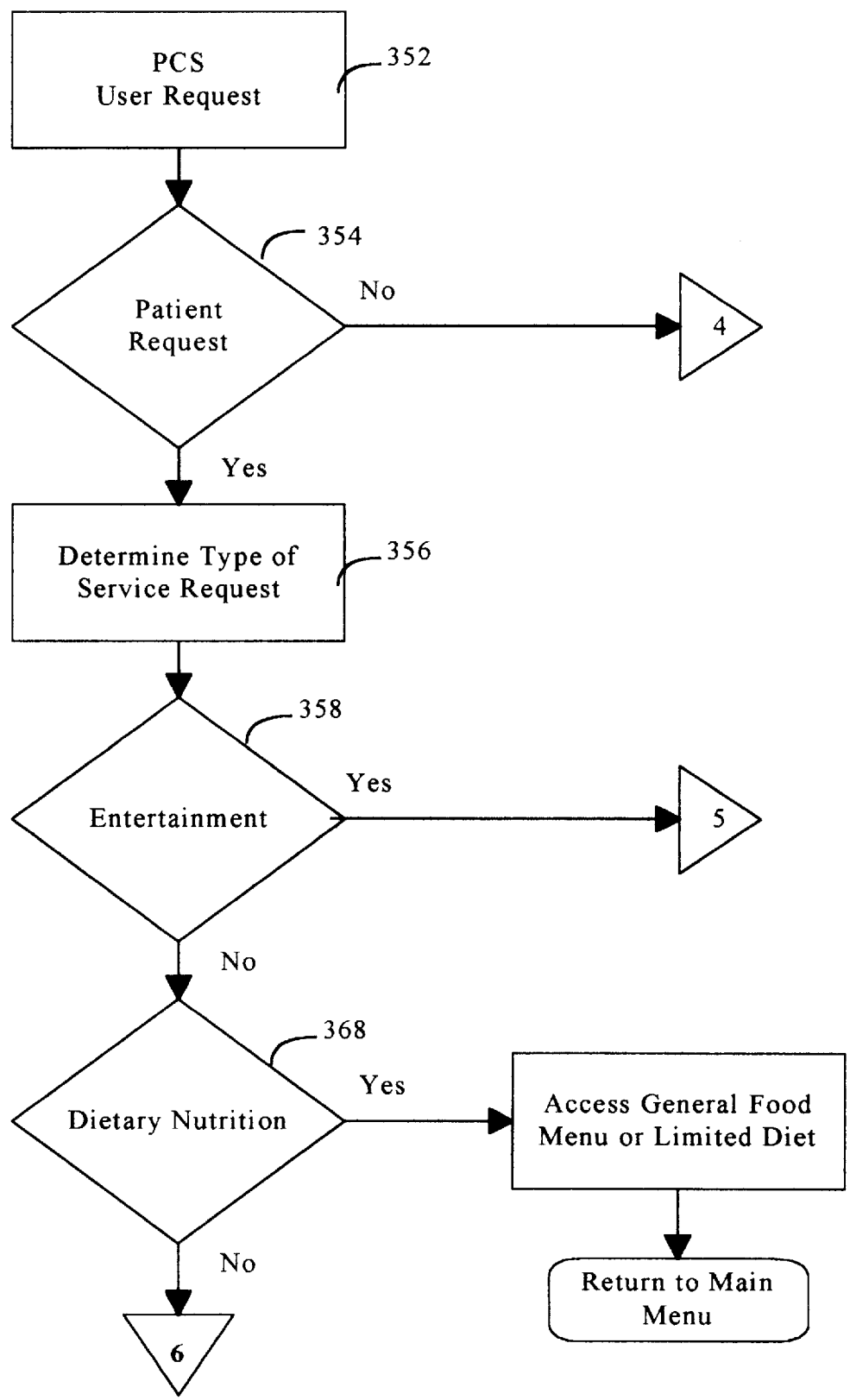
FIGS. 10A, 10B, 10C, 10D and 10E represent a flow chart that depicts the process a user (patient or medical staff) would perform in selecting various services from the internal medical information network.
Figure 10B:
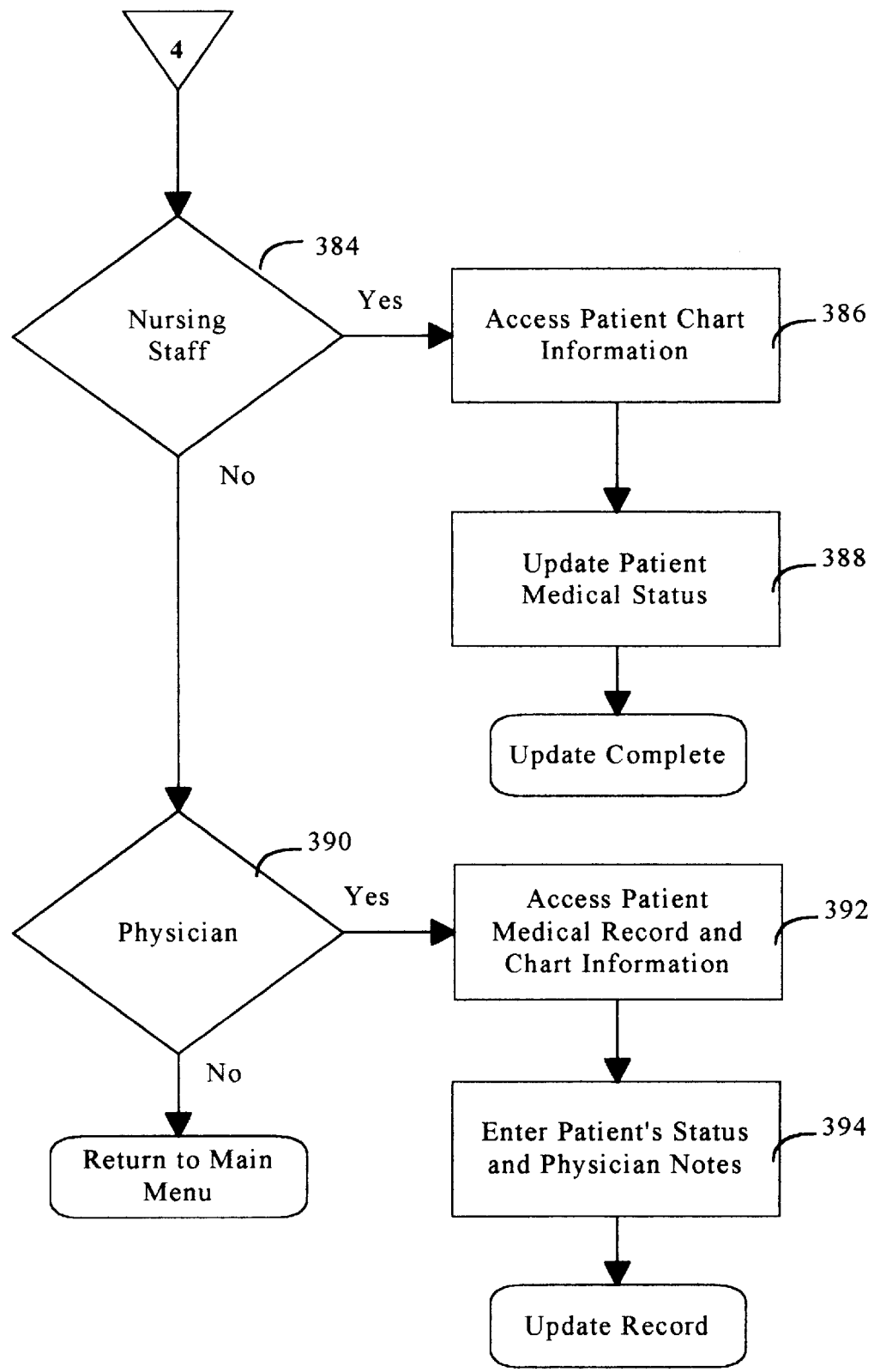
Figure 10C:
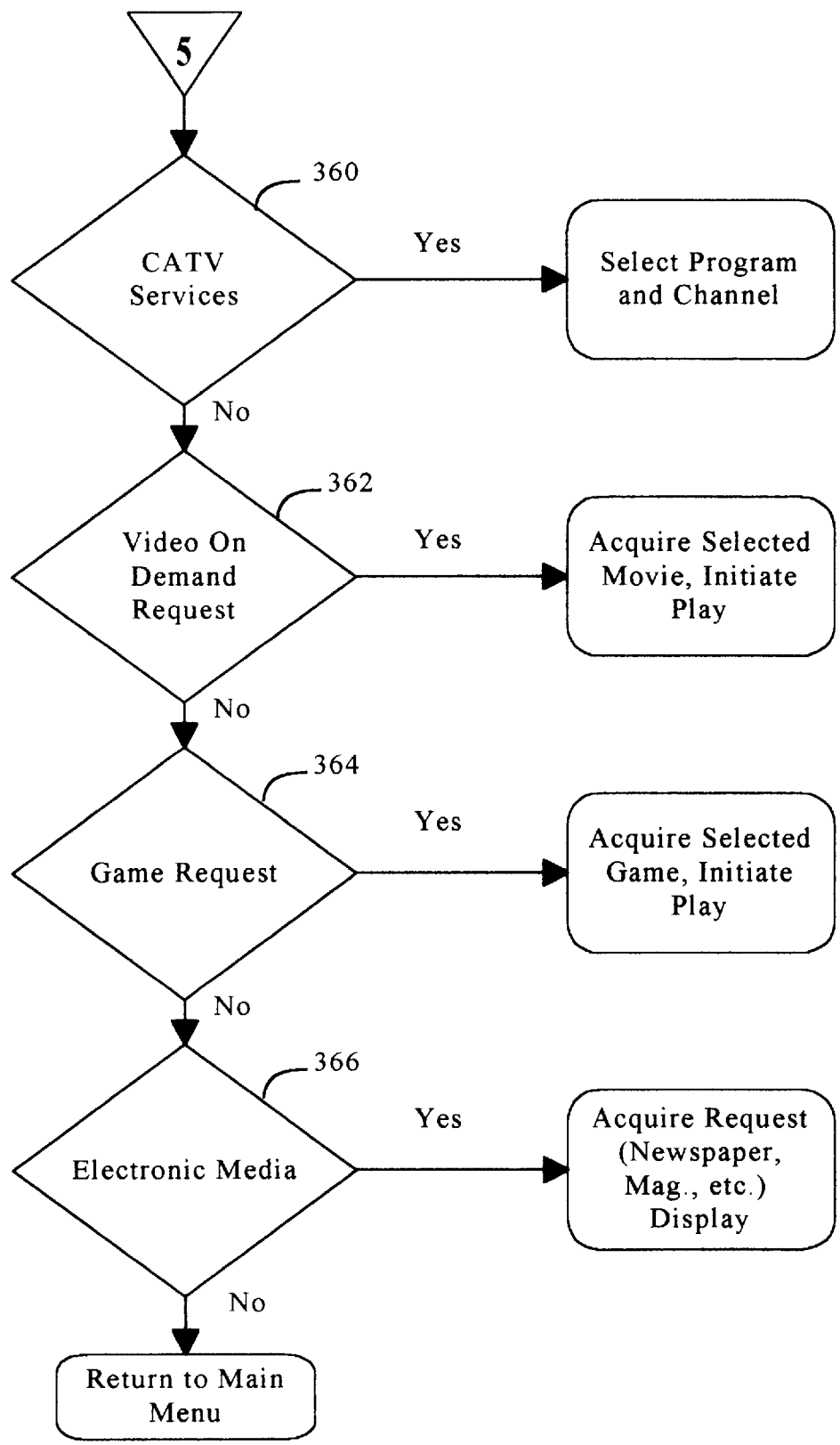
Figure 10D:
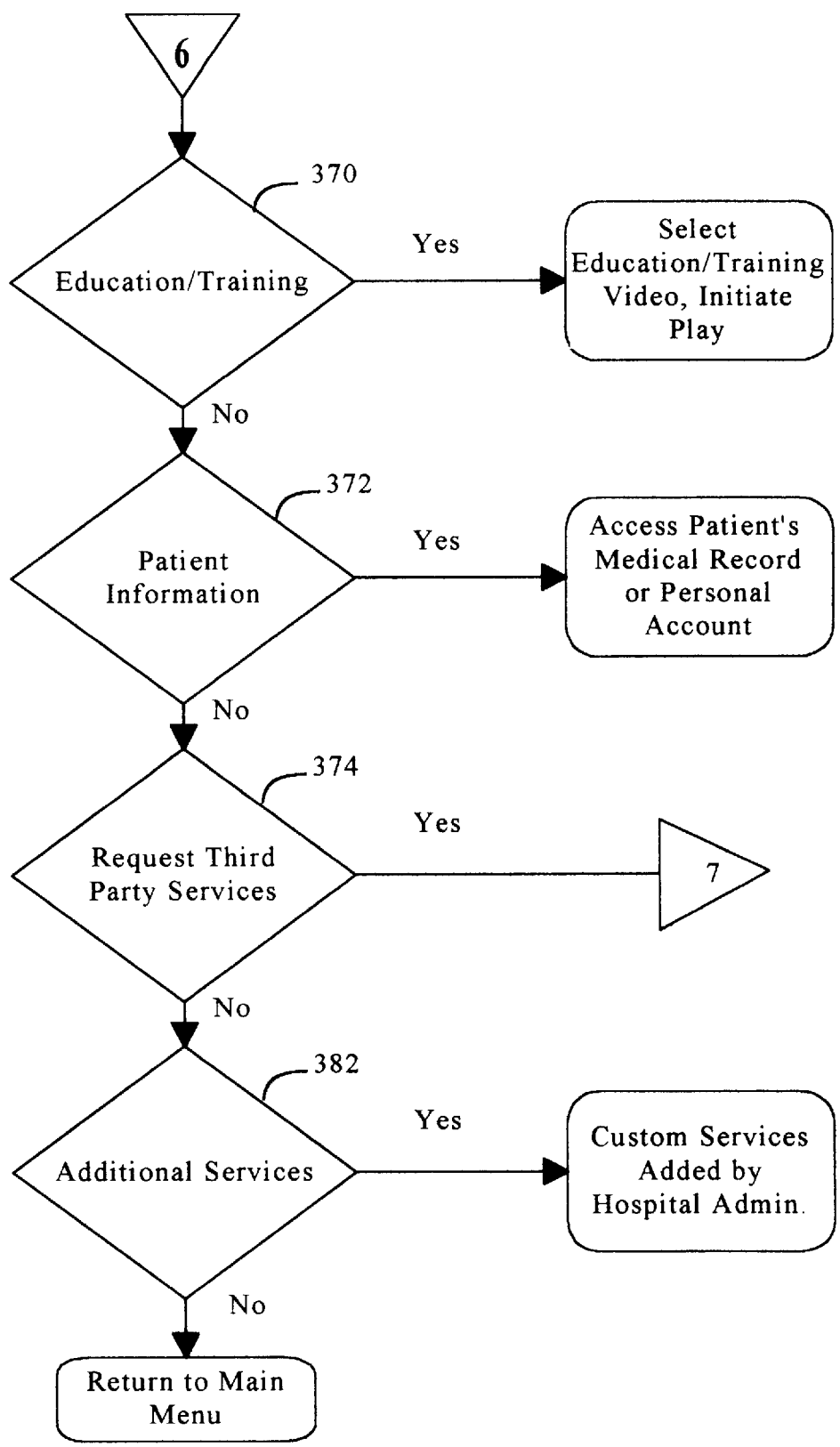
Figure 10E:
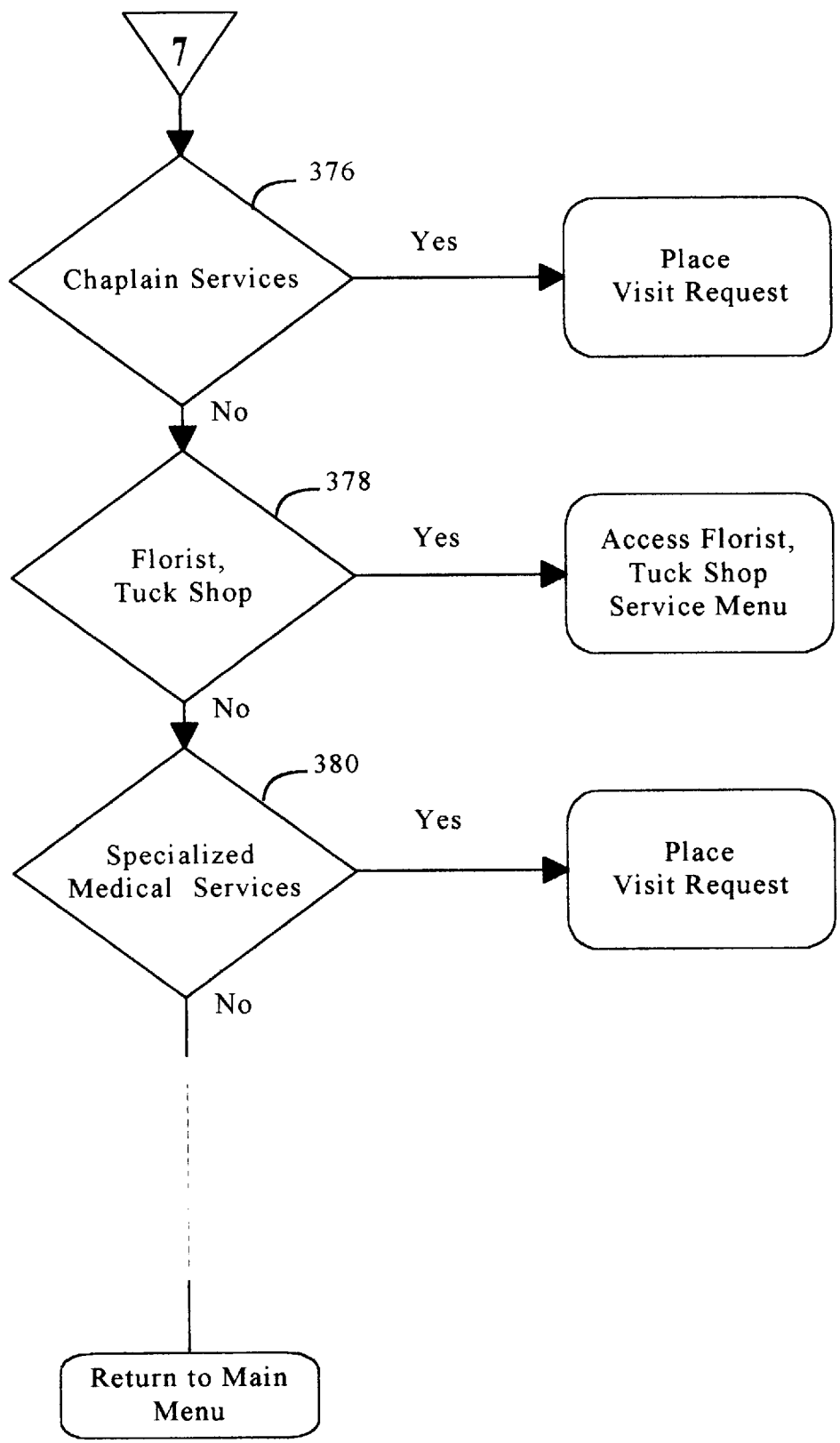
Figure 11A:
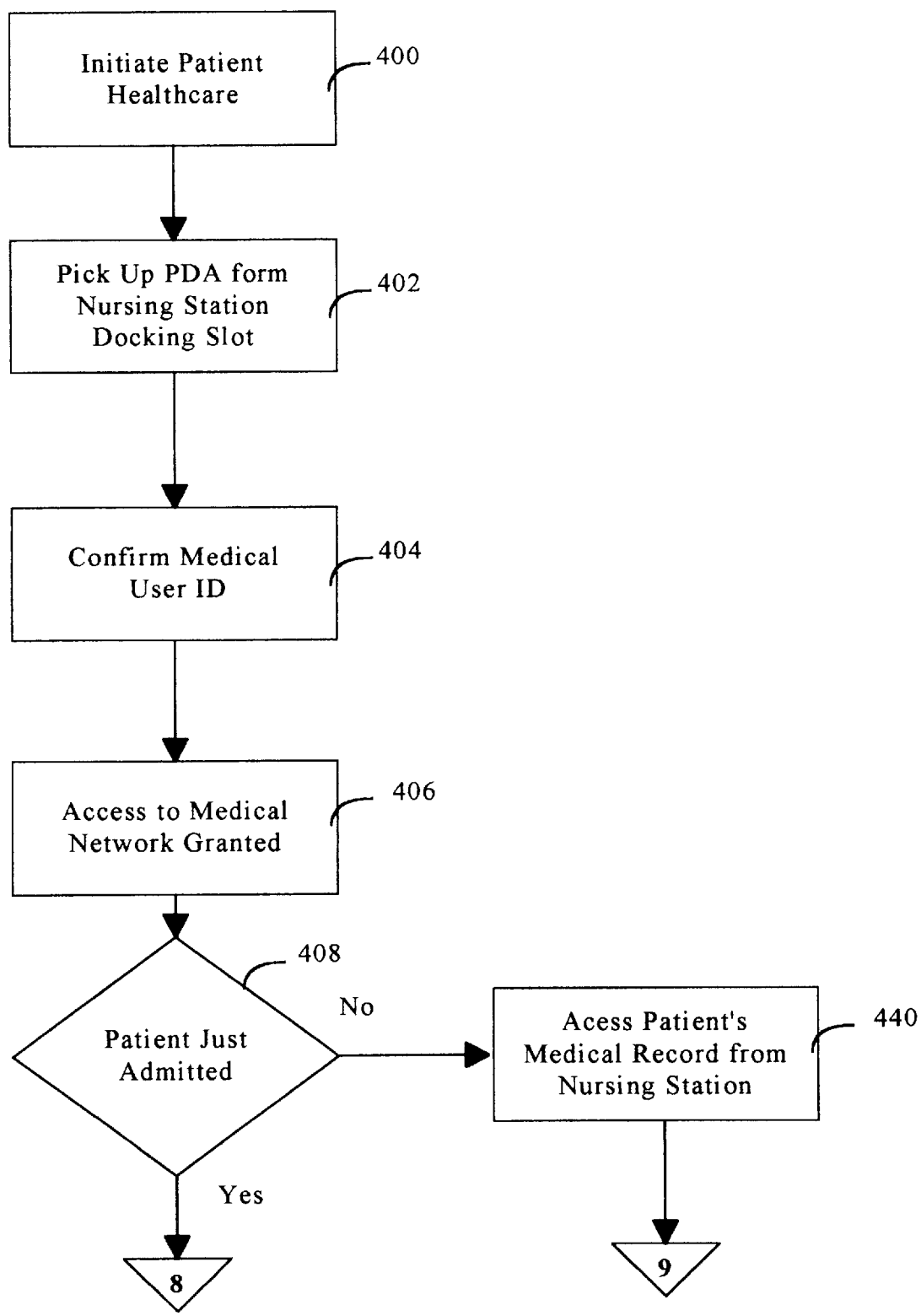
FIGS. 11A, 11B, 11C, and 11D represent a flow chart that details the process medical personnel would perform in the administration of health care.
Figure 11B:
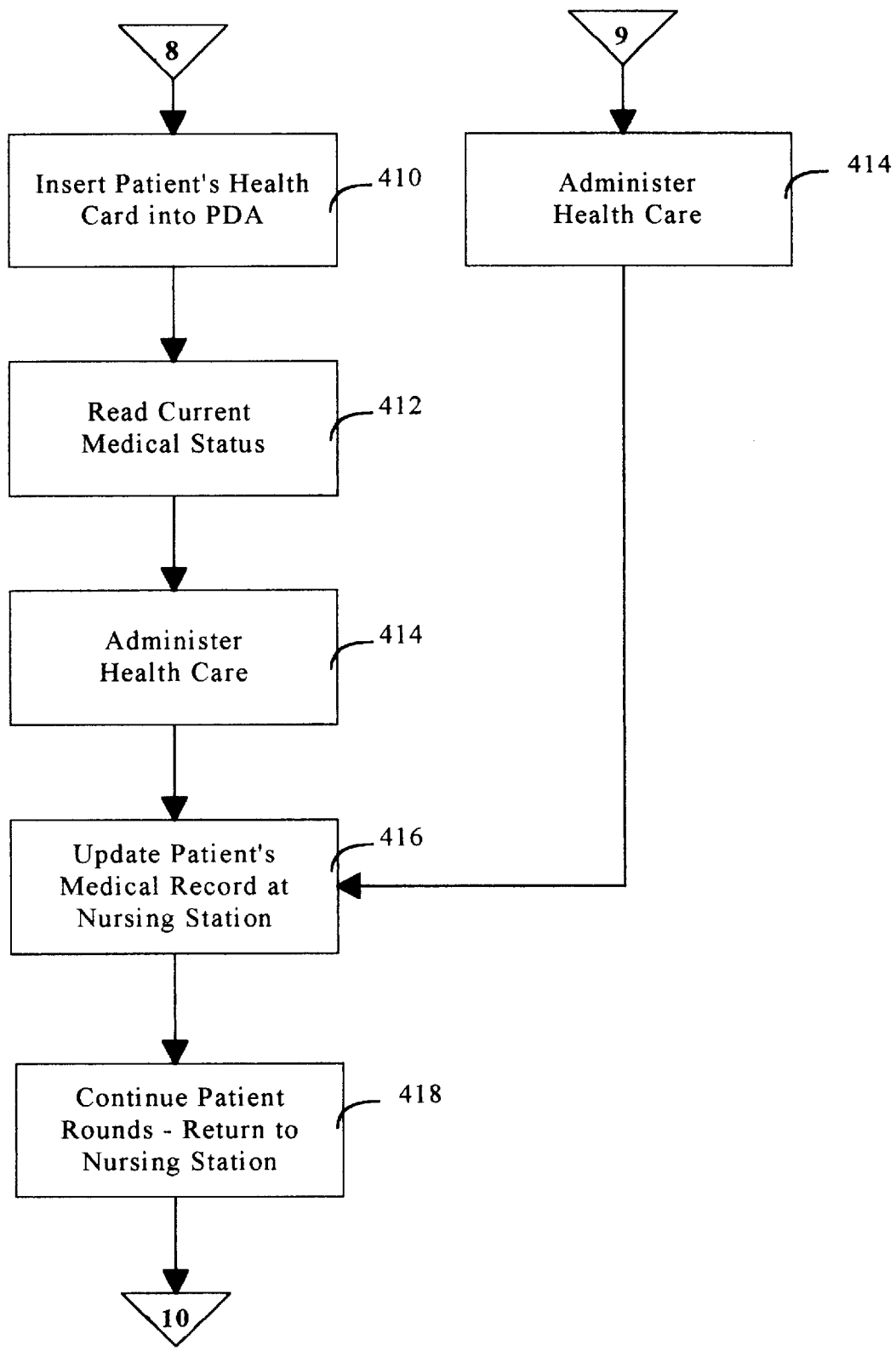
Figure 11C:
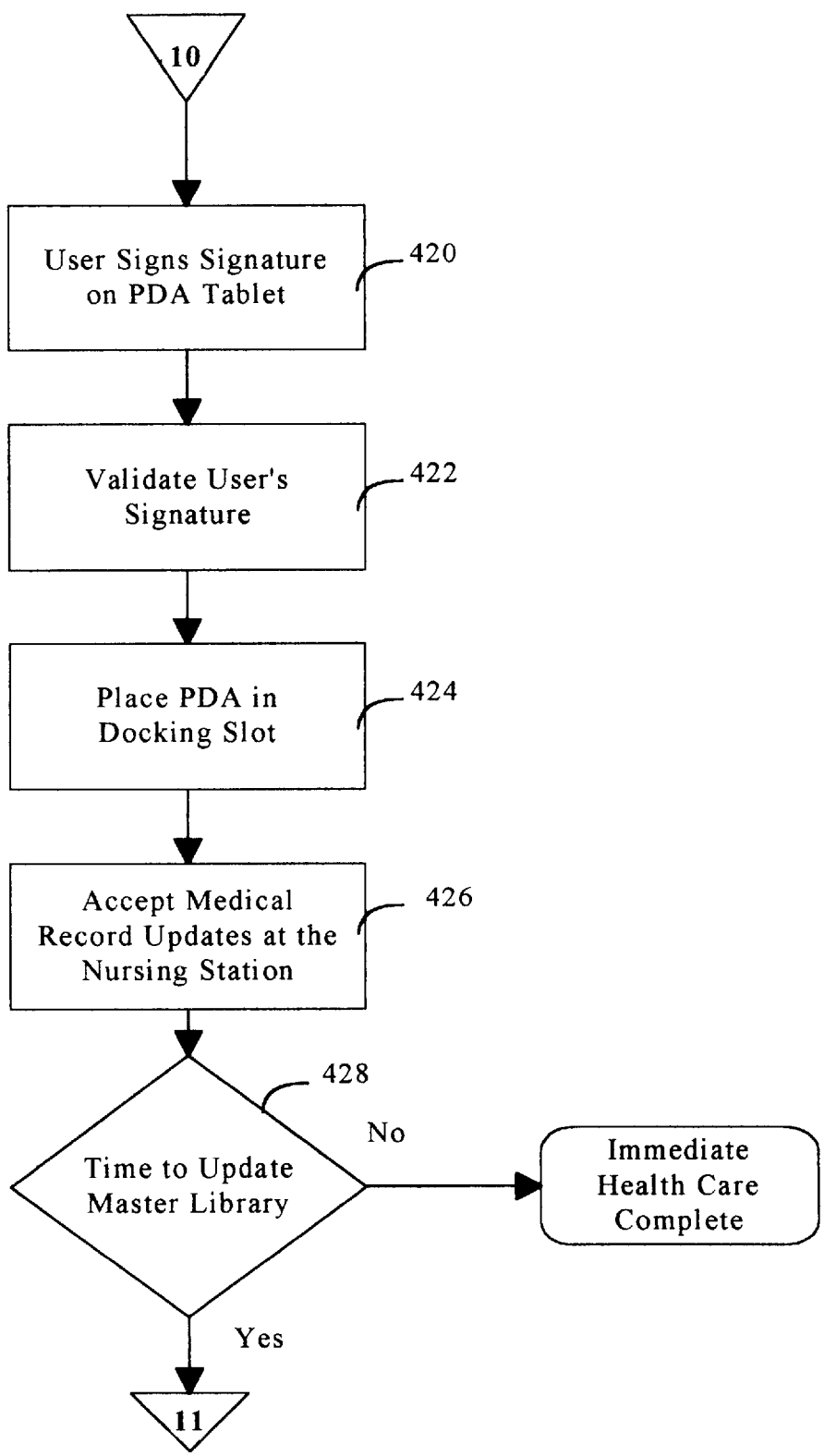
Figure 11D:
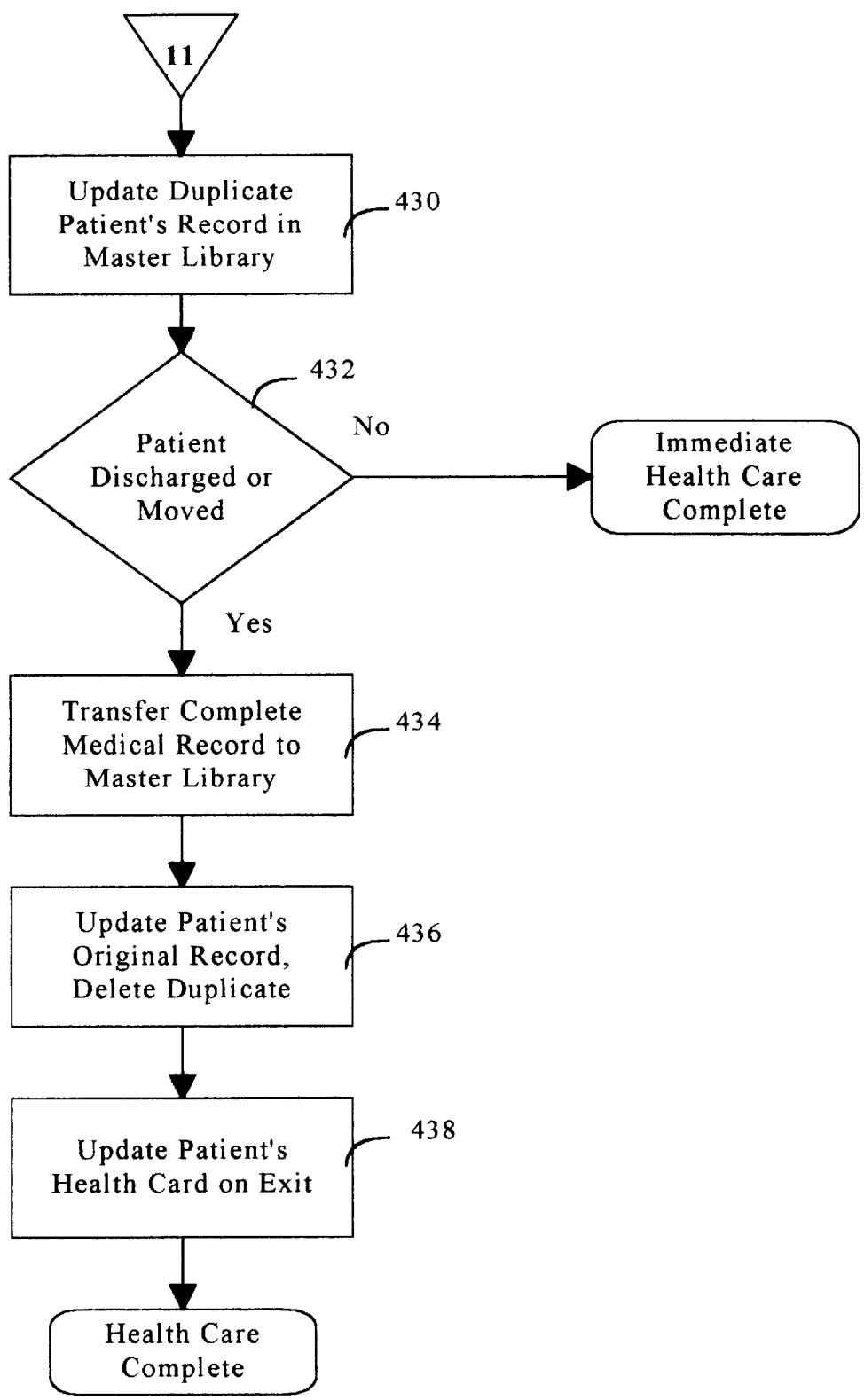

The complete ML is implemented within an unique security architecture (48). The security process is based on the identification and authentication of individuals requesting access to the health record database. This access can be requested internally or from external sources. Access is only granted to authorized users of which the library software automatically audits all users' accesses. Patients request or are sent a monthly statement illustrating who has had access to their health records. Various levels of security access are applied to different sections of the individual's health record i.e. psychiatric data can not be accessed by the general practitioner. The other aspect of the security shell deals with the data compression technology. Depending on the format of the data, different compression algorithms are used. This forms another level of security for without the correct decompression algorithm to undo the original compression operation, the data remains unusable. FIGS. 9A, 9B, and 9C illustrate the security screening access process that is implemented when a new user attempts to gain access (320) to the ML and the medical information network. Initially, each potential user of the network has completed a questionnaire that identifies who they are and specific demographics about them. Once successfully completed, an unique identification number (ID) is assigned to each user and their personal profile data is stored electronically online. Users are subdivided into specific categories relative to their qualifications, their professional status, and their necessity to gain access to medical information and/or the medical information network i.e. physicians as compared to nursing staff, ambulance personnel as compared to medical staff, surgeons as compared to psychiatrists, etc. To gain access to the medical information network, each user first enters their ID number (322). This ID number is then validated (324) with a central user list to confirm they are a legitimate user. If a match does not occur they are immediately denied system access (326). However, if a match is determined, the users personal electronic profile is accessed (328). The system then queries (330) the user with a specific question (332) i.e. What was your mother's name? If the user answers correctly (334), access to the network is granted (336) and the time of access is logged (344). This completes the user identification and authentication process. However, for each access attempt the user makes, the authentication query changes based on the information in the user's personal electronic profile. The validated user is now allowed to access the patient's electronic medical record. Depending on the category classification of user's ID number as previously discussed, general access (338) to the patient's record is granted or a further Personal Identification Number (PIN) is requested (340). This would occur in the situation where a patient's general practitioner would like to review the patient record to determine the latest status and would not have access to sensitive psychiatric data within the patient's record. This area could only further be accessed upon entry of another user's number (342) i.e. psychiatrist's unique PIN. As well as logging the access time of each user on the network, each patient record has its own audit trail. All authorised users that access any patient record, their name and time of access are all documented (344). The patient has the right to request an access log (346) for their personal medical record or the system can initiate a timely print out (348) of all active personal medical records which is forwarded to patient for review. When the authorised user has completed their requirement for accessing the medical network, a standard exit log-off procedure (350) is initiated If for any reason the user forgets to log-off the network, their access is automatically terminated after a duration of 12 hours.

Patient Care Station (PCS)

The PCS facilitates the interaction between the patient and ML services or between the medical staff and the ML.

Figure 4:
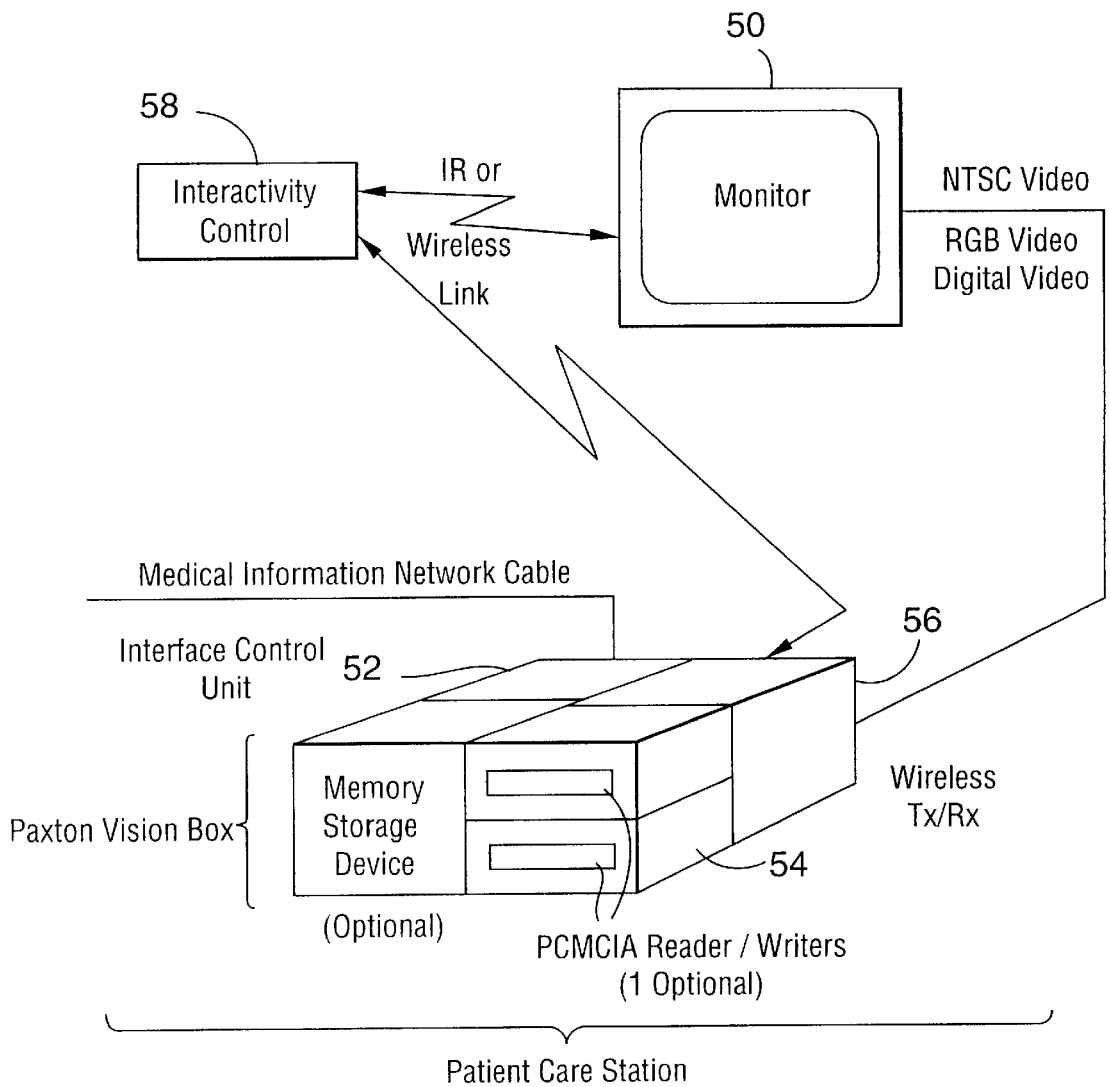
FIG. 4 is a schematic diagram of the apparatus and its manner interconnection to the other components of this system, of an example embodiment of the patient care station of FIG. 1.

Each PCS has an unique addressable identification code ensuring a one-to-one correspondence between the patient's location and the ML. The PCS has five main components (refer to FIG. 4): a monitor (50) that can display normal NTSC video, RGB video, or any other interlaced/non-interlaced digital video formats; an interface unit (52) to communicate with the medical information network; a Personal Computer Memory Card International Association (PCMCIA) reader/writer (54) or an equivalent smart card reader/writer technology; a wireless or Infra Red (IR) transmitter/receiver (56) to communicate with a Personal Data Assistant (PDA) such as those from NEC, AT&T, Apple, IBM, Fujitsu, etc.; and an input entry device (58) to facilitate patient/medical staff communication with the system (this entry device is either a remote or separate device or an integral component of the monitor).

Its operations are based around a user menu/submenu graphical interface which selects the desired/requested operation. Menu interaction is either effected through a touch screen on the monitor or through the remote interactive control device. Depending on the user, various menu formats are implemented. For the patient, a large graphical image is effected to facilitate the identification and selection of the requested service. For medical staff/physicians, a more detailed "Window" type menu is available to enable the selection of more detailed medical forms and services. The input entry devices, for these two types of users, are also different. For the patient, a simple numerical entry (the pressing of a single digit key button) to select the requested service would suffice, whereas the medical staff has a more sophisticated entry device to allow alpha-numeric data and features such as scrolling, cursor movement, etc. to be implemented. The interactive capability of the PCS allows the patient to order/select various services including meal selection, selection of a variety of entertainment packages including regular TV programming, movie videos on demand, video games, educational information, clinical data that the patient has been allowed to access, administrative information such as medical charges, and third party oriented services including those of the florist, chaplain, physiotherapists, etc. The data is transferred to and from the PCS in compressed digital format to minimize data loading on the network and then decompressed at the bedside when used. The decompression is accomplished via two means; the decompression algorithms are resident in the PCS such as the MPEG decompression technique for movie videos or the unique decompression algorithm is transmitted with the data file when transferred to the user. This is the situation when specific lossless compression techniques are used in the processing of medical files relating to high resolution images i.e. MRI or X-ray video data. FIGS. 10A, 10B, 10C, 10D and 10E represent a flow chart that depicts the process a user (patient or medical staff) would perform in selecting various services (352) from the internal medical information network. The PCS and its associated monitor/TV, when in the idle mode, displays on the screen a simplistic graphical interface which categorizes the user as a "patient" or as "medical personnel". When the user is classified as a patient (354), a sub-menu appears identifying all the services (356) that are available at the bedside. These include the following specialities (though not limited to), which are selected by a simple numeric designation:

1) Entertainment (358)—further subdivided into
   a) cable TV programming (360)—channel selection
   b) video on demand movies (362)
   c) interactive games (364)
   d) electronic media including newspapers, magazines, etc. (366)

2) Food/Dietary menu (368)
3) Educational/Training information (data and video material) (370)
4) Personal Patient information (372)
5) Third Party Services (374)—further subdivided into
   a) chaplain visit requests (376)
   b) florists, tuck shop, convenience store, etc. (378)
   c) medical services such as physiotherapy (380)
6) Additional Services (382)—custom requirements If the user has been classified as "medical personnel", they initially enter their unique ID number to further classify them as nursing staff, or practising physicians. If nursing staff (384), the patient record information is retrieved from the appropriate nursing station and the associated patient charts and data entry forms are displayed (386). The correct information is then entered i.e. temperature, blood pressure, medication administered, etc. and then the patient's medical record is updated (388). If the user has been identified as a physician (390) then the entire medical record (392) is made available for viewing at the bedside through the PCS. The physician then enters their personal notes, observations, etc. (394) and the patient's medical record is modified accordingly. It should be noted that no mention has been made as to the specifics of the data entry device: this can either be accomplished directly through a touch panel on the display or through a personal data assistant as will be discussed subsequently.

Figure 5:
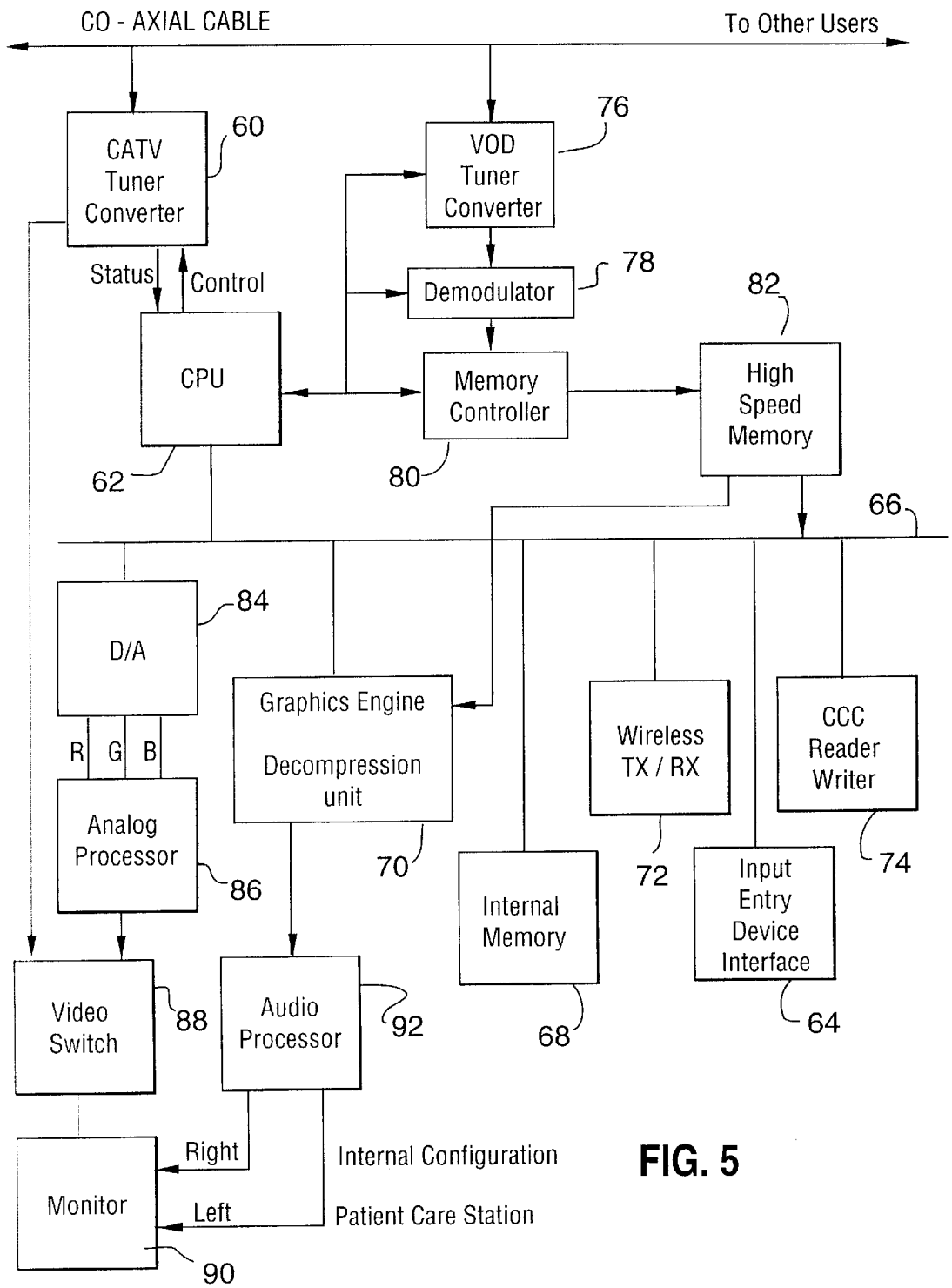
FIG. 5 is a schematic block diagram of the internal configuration of the patient care station of FIG. 4.

With reference to FIG. 5, for the preferred HFC cable implementation of the medical information network, normal CATV signals are received by the PCS through the CATV tuner/convertor (60) and routed directly to the monitor for display. Control of the CATV tuner is performed by the CPU (62) that has received its instructions (i.e. channel selection) from the input entry device interface (64). This input entry device interface unit is either an integral part of the monitor such as a touch screen or a separate component of the PCS as previously described. The CPU is also connected to an internal bus (66) that handles data transfer and control/status signals which links internal memory (68), a graphics/decompression processor (70), the wireless transmitter/receiver for the PDA interface (72), and the PCMCIA reader/writer unit (74). A complementary RF tuner/converter (76) exists for the Video On Demand (VOD) requests. The CPU controls the channel and movie selection of the VOD tuner which routes the data to the demodulator (78) to restore the original digital data stream. A specific memory controller (80) is used to control the data (compressed video information) passed to the high speed memory device (82) that is either magnetic, optical, (or combinations thereof), or solid state (includes flash card memory) depending on the amount of data transmitted. Upon playback, the compressed data is first decompressed by the decompression unit (70) and than processed by the D/A converter (84) and analog processor (86), depending on the video format to be displayed, and passed to the monitor (90) through the video switch (88). The audio (stereo) is processed by a separate processor (92) fed directly from the decompression unit.

The health card reader and/or writer that is a major component of the PCS is based on smart card technology. This reader/writer supports various configurations of smart card technology be they based on solid state memory and microcontrollers (Hitachi, Motorola, SGS-Thomson, Bull, Catalyst, etc.), optical memory (Drexler, Canon), or combinations of the aforementioned. The standardized PCMCIA card slots are utilized. These cards are used to maintain an electronic health record or other user information in digitally compressed format on each patient. These cards are appropriately modified and updated as health care is administered. The health card, by default, allows the network to track the location of the patient through the unique address ID of the bedside PCS and the uniqueness of the patient's health card. Therefore the system always knows the exact location of each patient at all times even if the patient is moved, for as soon as the patient's health card is inserted in the smart card slot of another PCS, the network registers this initialization automatically. As long as the patient is at this bed location, their health card remains inserted in the associated bedside PCS.

Because the PCS utilizes a coaxial cable interface, the PCS can be located at the residence of the patient. This facilitates the out-sourcing of health care to external health care service providers. The PCS receives from the ML post recovery rehabilitation information in the form of video and text data, special dietary/nutrition instructional data, physical rehabilitation programming, etc. The PCS also interfaces with specific external health care monitoring equipment to register and track certain patient characteristics as temperature, pulse rate, etc., then pre-processes the data, and transmits the results back to the ML. Video monitoring of the patient's condition is also facilitated through the addition of a remote small video camera. By means of a PDA carried by an external care giver, detailed health record information is accessed from the ML and modified with up-to-date medical diagnostic data.

The monitor is either that of a Cathode Ray Tube (CRT), Liquid Crystal Display (LCD), or newer technologies such the diamond-based video and computer display panels. The display is either interlaced or non-interlaced depending on the display technology used. The monitor, as a preferred configuration, will have the hardware functionality and associated resident software in the display driver to facilitate Display Power Management Signalling (DPMS). This feature has the capability to place the monitor into four different power states: on, standby, suspend, and off, depending on the activity of the PCS. This will result in significant energy savings, especially during periods of relative inactivity, where the monitor is placed in an efficient power mode.

Several options exist with respect to the PCS. Additional PCMCIA slots can be added to facilitate features such as FAX/modems, expanded memory requirements, special interfaces to local area network systems i.e. DEC Ethernet, etc. The PCS can also be equipped with a simple magnetic stripe card reader and/or writer to accommodate other types of health cards. Voice recognition software/hardware (such as the technology available from Kurzweil) can be added to facilitate the entry of health record information via voice. Included in this feature would be the use of an individual personality PCMCIA card, to customize the voice recognition software to the individual's unique voice attributes. This eliminates the need to train the voice recognition software which could take a sufficient length of time and likely lead to significant errors during this training period.

Computerized Nursing Stations

Based around a distributed processing network, each nursing station consists of a client/server configuration with internal memory (CD-ROM, magnetic disk, or solid state RAM) to temporarily store the entire health records (in compressed format) for the patients who are resident in the beds monitored by this station. This distributed computerized nursing station is dedicated to a complete hospital wing, or several wings but only controls/monitors a specific number of beds. It is also the centralized location for the PDA docking slots that are interfaced to the nursing station processing unit. A copy of the patient's medical record is maintained at the nursing station until the patient is either moved or discharged. The medical records are downloaded from the ML in compressed format after the patient is admitted to a bed monitored by the nursing station. The ML knows the location of the patient through the unique association of the patient's health card which has been inserted into the bedside PCS, the PCS identification code, and the nursing station/bed hospital architecture.

Refer to FIGS. 11A, 11B, 11C, and 11D, a flow chart that details the process medical personnel would perform in the administration of health care (400), when reading the following description. When care is to be administered, the medical staff picks up the PDA from its docking slot (402) at the nursing station and carries it with them to the appropriate room. Access through confirmation of the user's ID (404) and modification to the patient's electronic medical record is performed through the authorized medical staff's secure signature pen (100) and the PDA display tablet (100) (refer to the next section on Medical Personal Data Assistant) once access to the network has been granted (406). Initially, upon admittance (408), the patient's health card is inserted into the PDA (410) to determine the patient's present (or most recent) medical status and any further supporting medical history data that is relevant (412). This is necessary because even though the patient's medical record has been transferred from the ML to the appropriate nursing station, additional health care may have been administered since the latest update to the patient's archived record i.e. ambulance personnel, on the way to the hospital, could have administered medication which has been documented on the patient's health card. If the patient is already under care in the hospital, the patient's medical record is simply accessed from the nurse's station (440.). The medical personnel then updates the medical record in accordance with the administered health care (414). The PDA automatically transfers the modified health record or portions thereof to the PCS via the wireless/IR communications link (102). These timely updates are conducted in digitally compressed format and the modified data is transferred to the appropriate nursing station (416) and linked with the patient's complete medical record temporarily located here. This periodic updating ensures that the health records are maintained in a timely and efficient manner and resolves the issue that the PDA may be separated from its docking slot for a long period of time due to the possibility of other medical emergencies that require the attention of the administering medical personnel.

When the physician or nursing staff return to the nursing station (418), the medical personnel signs their signature on the PDA tablet display (420) with their personalized signature pen. Validation of their signature (422) with the pen's internally stored master signature, authenticates that 1) this individual is an authorized user and 2) that the changes to the health record(s) can now be formally accepted by the nursing station server system. The PDA is placed in a docking slot (424), and the health record(s) data that has been transferred previously to the nursing station is checked for completeness (all modified data pertaining to any patient's health record have been transferred) and that these modifications can now be officially accepted (426). If there is additional data to transfer, this is accomplished automatically in compressed format through the wireless or infra red communications link, integral with the docking slot. The PDA's battery pack is also recharged when placed back in the docking slot. The PDA is then officially declared free for use again by other medical staff. Periodically, the ML is also updated (428) with the most recent health care status for each examined patient. The data within the health records are compressed first before transmission to the ML. This modified data is held in a temporary record file (430) separate from the original health record though linked to it. This periodic updating of the ML facilitates the capability of external users, such as general practitioners, to access their patient's files to determine the latest health care status. This periodic update time is entirely programmable, and will vary from hospital to hospital, dependent on administrative policy.

The modified electronic health records are maintained at the nursing station until the patient is discharged from the hospital or moved (432) to another location that is controlled by another nursing station. Upon patient discharge, the patient's complete updated electronic health record is transferred back to the master library (434) in compressed format and replaces the original record resident there (the original record is replaced with the new one and the temporary record file destroyed) (436). If hospital policy dictates that past records are to be kept or changes to the original be archived, the original health records are stored as well. When the patient is discharged from the hospital, at the last control point, their health card is updated (438) with the particulars of the most recent administered health care. This is accomplished through a health card writer device that is present at this discharge location. The health card always remains with the individual to facilitate home health care services with medical personnel that may administer health care externally from the hospital.

Because the electronic health record is based on pre-established formats that are resident in the PDA (especially nursing charts), it is very easy to determine changes or additions to patient health records that contain the original information. Changes to patient medication or care are easy to determine through software comparison means, and as a result the nursing station server extracts this information and automatically indicates to the nursing staff, changes that have occurred with respect to the patient's administered care. As a fail safe check these changes are highlighted at the nursing station. The nursing staff acknowledges that these changes have been recognised by entering an acknowledgement check in the patient's modified health record.

Medical Personal Data Assistant (PDA)

The PDA (100) will replace the paper clipboard and allow the user to interface to an electronic database. Patient information is loaded to/extracted from the PDA. All the information passed to/from the ML or the nursing stations is in data compressed format thus enabling the transfer of video images i.e. X-rays to the bedside PCS. The following items identify specific features that are functions of or available options that make this PDA technology especially suited for this application:

(1) conversion of hand written material into neat text with word processing features to edit what has been written.

(2) electronic table of contents facilitating ease of data search and retrieval. Integral medical forms facilitating data entry.

(3) interface with a separate docking unit where information is exchanged between the pen based computer and the distributed processor at the nursing station. This is accomplished through an infra red or wireless communications link. Recharging of the integral battery pack is also implemented when the pen based computer is resident in the docking slot.

(4) voice annotation to modify or correct pen entered data. Voice entry through a head set or through an embedded microphone would effect a hands free data entry operation.

(5) built-in paging capability to receive messages from an external source, i.e. hospital emergency services.

(6) an integral PCMCIA slot(s) that enables the interface with the health card and any other PCMCIA compatible cards.

Figure 6:
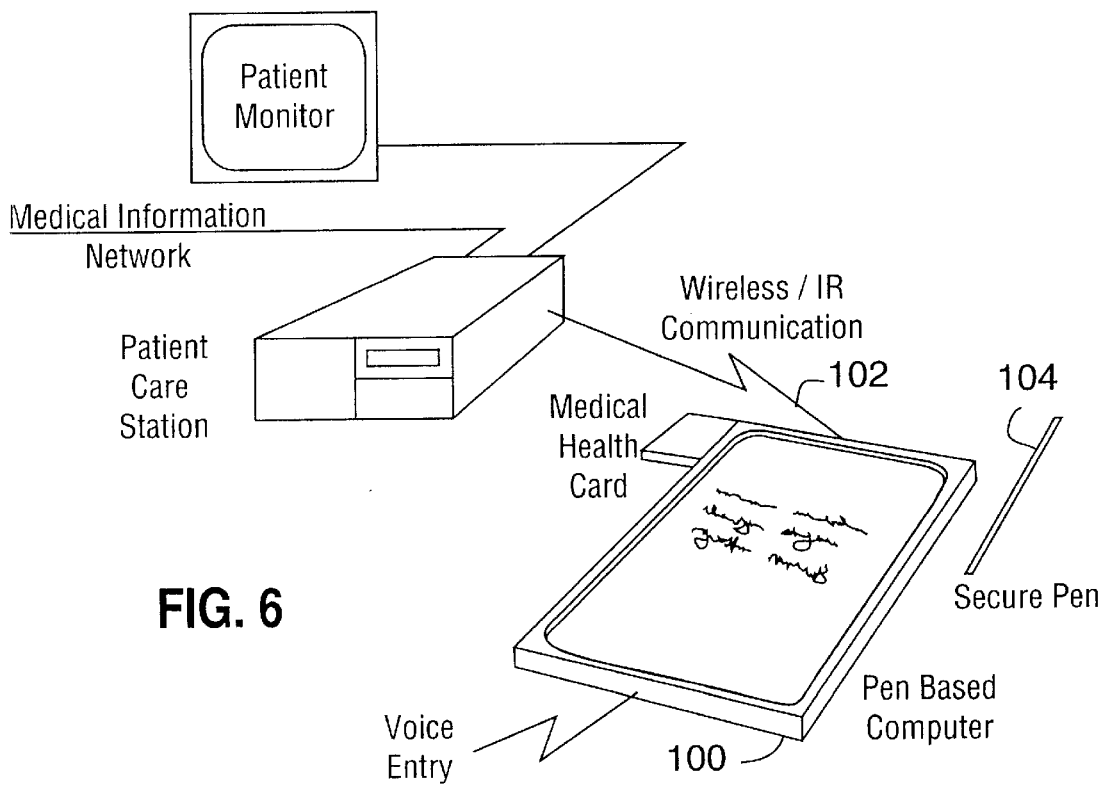
FIG. 6 is a schematic view of an example embodiment of a system for patient information input, as well as access and retrieval of that information, in accordance with the present invention.

To enable interaction with the electronic medical record resident on the patient's health card or the stored patient record transferred from the ML to the appropriate nursing station, pen based computer or Personal Data Assistant (PDA) technology (100) is utilized (reference FIG. 6). Each PDA has been assigned a software identification code that is continuously monitored while the PDA is resident in its docking slot located at the nursing station. This PDA technology contains PCMCIA slot(s) that are used to read and/or update the patient's health card. When the health card is read, the data is suitably decompressed before viewing on the PDA. When health care is to be administered, the patient's health card is inserted in the pen based technology and the health status/history viewed. The examining personnel then adds to these electronic medical records, via the PDA technology, in accordance with the present diagnosis or medical status update i.e. the present examination data area is modified. This new information is entered through the PDA technology by simply writing as normal on the pen display tablet or entering information into pre-defined electronic medical forms or charts. If further information is required that is not resident on the patient's card, the patient's medical record temporarily stored at the nursing station is accessed through the patient's PCS to acquire further data. This information is transferred in digitally compressed format from the nursing station to the unique PCS that has requested the additional information and then further onto the pen based system via wireless communications or broadband IR communications (102). The additional information is then decompressed for viewing purposes. If this additional information has been that of a high quality medical image, the PDA requests the viewing of this data on the patient's monitor to take advantage of its enhanced resolution. In the case where medication has been assigned, a validity check is performed against any present patient medication (as indicated in the emergency data area of the health card), to ensure against medication incompatibilities. This check is accomplished with respect to a pharmaceutical database maintained in the ML.

Figure 12A:
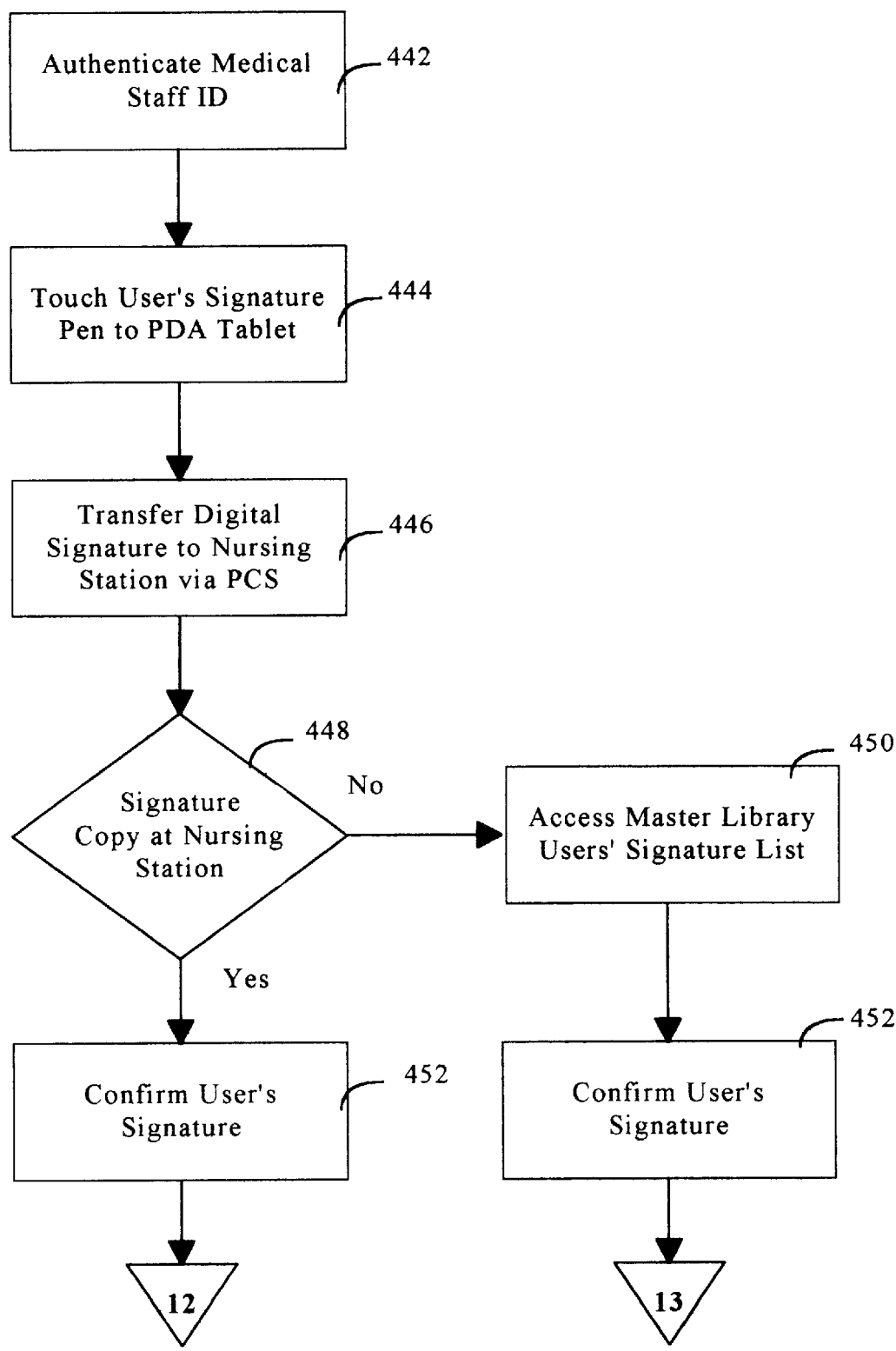
FIGS. 12A and 12B represent a flow chart that describes the identification and verification process that occurs when medical personnel initially attempt to gain access to the internal medical information network for the use of and modification to patient's electronic medical records.
Figure 12B:
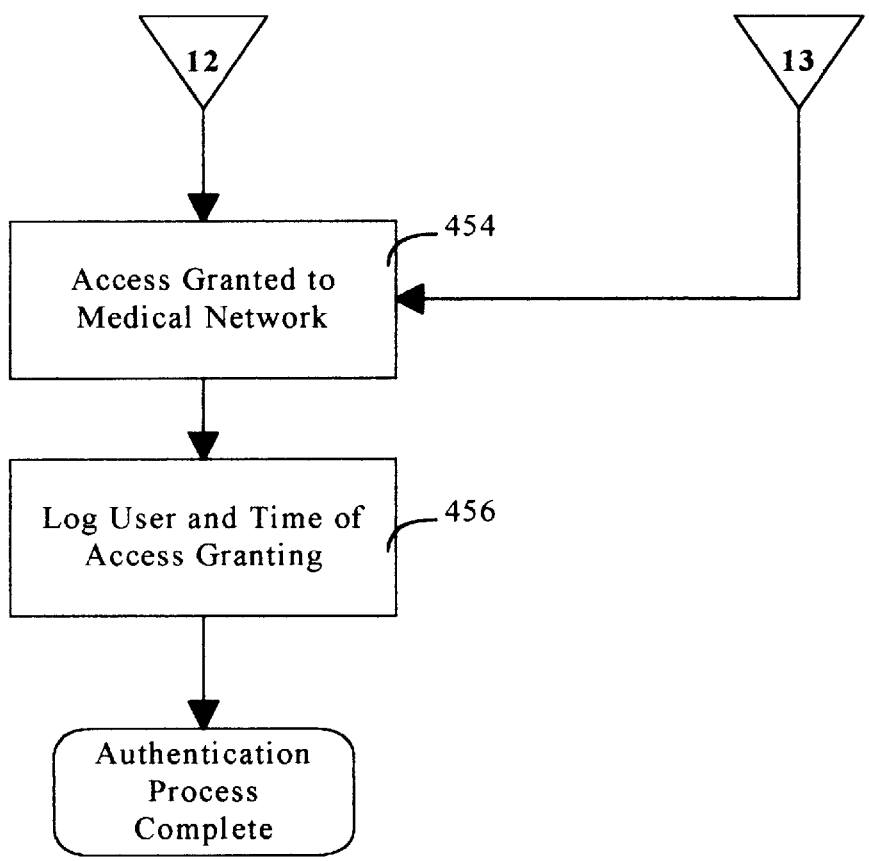

FIGS. 12A and 12B represent a flow chart that describes the identification and verification (442) process that occurs when medical personnel initially attempt to gain access to the internal medical information network for the use of and modification to patient's electronic medical records. To ensure authorized personnel are only allowed access to the internal medical information network, a secure signature pen (104) is used. This is an unique pen or stylus which each user is allocated in order to access medical information through the network This pen contains an internal memory (Dallas Semiconductor) with an encrypted replica of the personal signature of the medical personnel, which once validated by the system, allows access to the network. This replica of the user's personal signature is stored in the signature pen's internal memory in digitally compressed format that is transferred to the PDA when the pen is initially touched to the PDA tablet (444). Personnel signature data files of all authorized users using that particular nursing station are stored on location at the nursing station's file server system for validation purposes. The user's signature replica, having been stored in the PDA, is transmitted to any PCS located at the bedside through either the wireless or broadband IR communications link (102) and then relayed onto the nursing station (440) where it is decompressed for comparison validation purposes. This transfer process of the user's signature replica will usually occur at the first patient's bedside that the medical personnel (nursing staff or physicians) is administering health care to. If a comparison match does not occur after searching all the stored signatures at the nursing station (448), a search of the master signature list (450) within the ML is initiated. This occurs when a visiting specialist, likely located in another region of the hospital, is administering health care to a patient that is not resident in their area. The master signature list at the ML however, contains signature data on all authorized users for the overall hospital. Once validation has occurred (452), an indication is transferred to the ML administrative software management system that network access has been granted to that user (454). There is established an unique one to one relationship between the medical personnel, due their digital signature, and the PDA because of its software ID. This facilitates the establishment of an unique audit trail for the network by tracking the authorized personnel granted access and at what time this access was initiated (456).

All the appropriate standardized medical forms are stored in the PDA's memory and accessed through a simple menu window. Custom forms are capable of being generated if required. The data entry is kept to simple operations to reduce the amount of handwritten text to minimize errors and enhance performance. Each time the PDA is loaded into its docking slot located at the nursing station its software clock is synchronized with the clock of the master library. This ensures an accurate time audit trail being associated with each patient's health record as to when it was changed/updated and automatically entered into the master library. The PDA also has the capability of containing a paging unit eliminating the need for medical personnel to carry a separate paging device. Personal messages are routed to the appropriate medical staff because the system, through the unique one to one relationship established between the user's pen and the PDA, knows the location of that individual.

Electronic Medical Records

Integrated with the PCS as previously mentioned, is a smart card reader/writer unit. The intent is to provide a complete electronic medical record in digital compressed format supplying as much medical information on the patient as possible i.e. blood type, vaccination and medication data, diabetic controls for blood sugar levels, allergy data especially when drug related, etc.

The health card's memory is to be divided into explicit regions.

(1) Personal Data—personal ID that contains a video compressed image of the individual to authenticate the user, other personal data (name, address, next of kin, date of birth, etc.), insurance coverage, etc. Once user verification has been ascertained, access to the remaining medical data is granted.

(2) Emergency Data—contains data of life saving importance i.e. blood type, allergies, any medication, immediate medical history relating to patient status such as diabetes, Parkinson's disease, dialysis treatment, etc. This data is available to anyone who has a card reader unit such as in an ambulance or carried by a home health care service individual.

(3) Medical History—contains the medical history of the patient including past diseases, injuries, operations, etc. and associated treatments. This area, once access has been granted through item 1), is further sub-divided into medical disciplines i.e. general practitioner data, specialist and surgeon data, psychiatric data, etc. each accessible by only those authorized to its access. Pertinent video images relating to radiology, X-rays, etc. are stored through digital video compression techniques.

(4) Present Examination Data—documentation of the actual examination, who performed it, where and when, and the diagnosis with the prescribed medication, if any. This area is automatically entered into the medical history area when a new examination occurs. A comparison of past examinations can be performed to determine if the patients state of health has improved or deteriorated.

The entire operation (access and data retrieval) with respect to the use of the health card, is protected with a security envelop. Medical data is fully encrypted, data integrity is assured, access is rigidly controlled, and access audit trails conveniently maintained.

The following items/systems can be considered as preferred options to the master library, the medical information network, and the PCS.

The Regional Medical Library

Figure 7A:
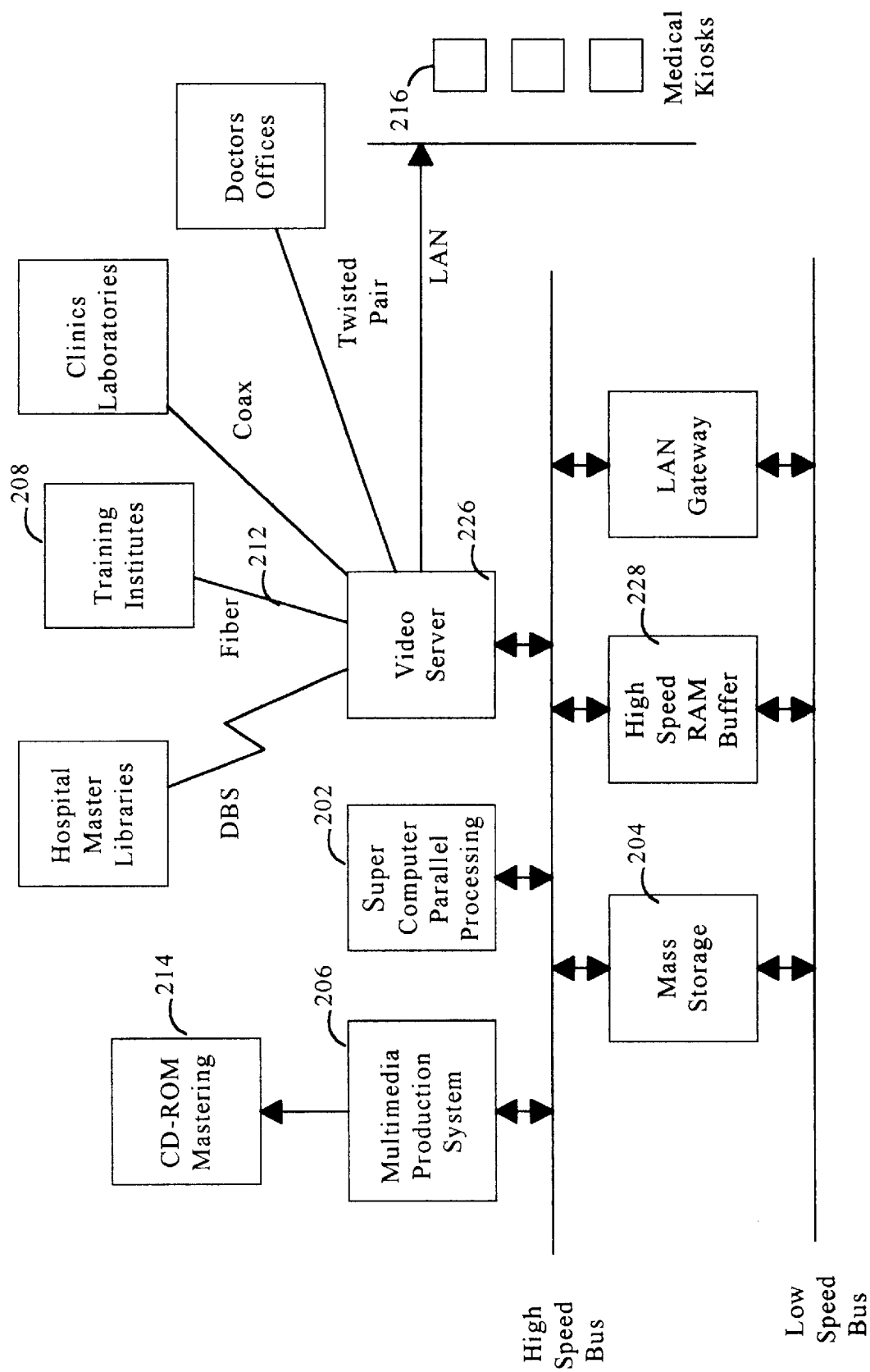
FIGS. 7A and 7B are schematic views of an example embodiment of a configuration of the regional library of FIG. 1.
Figure 7B:
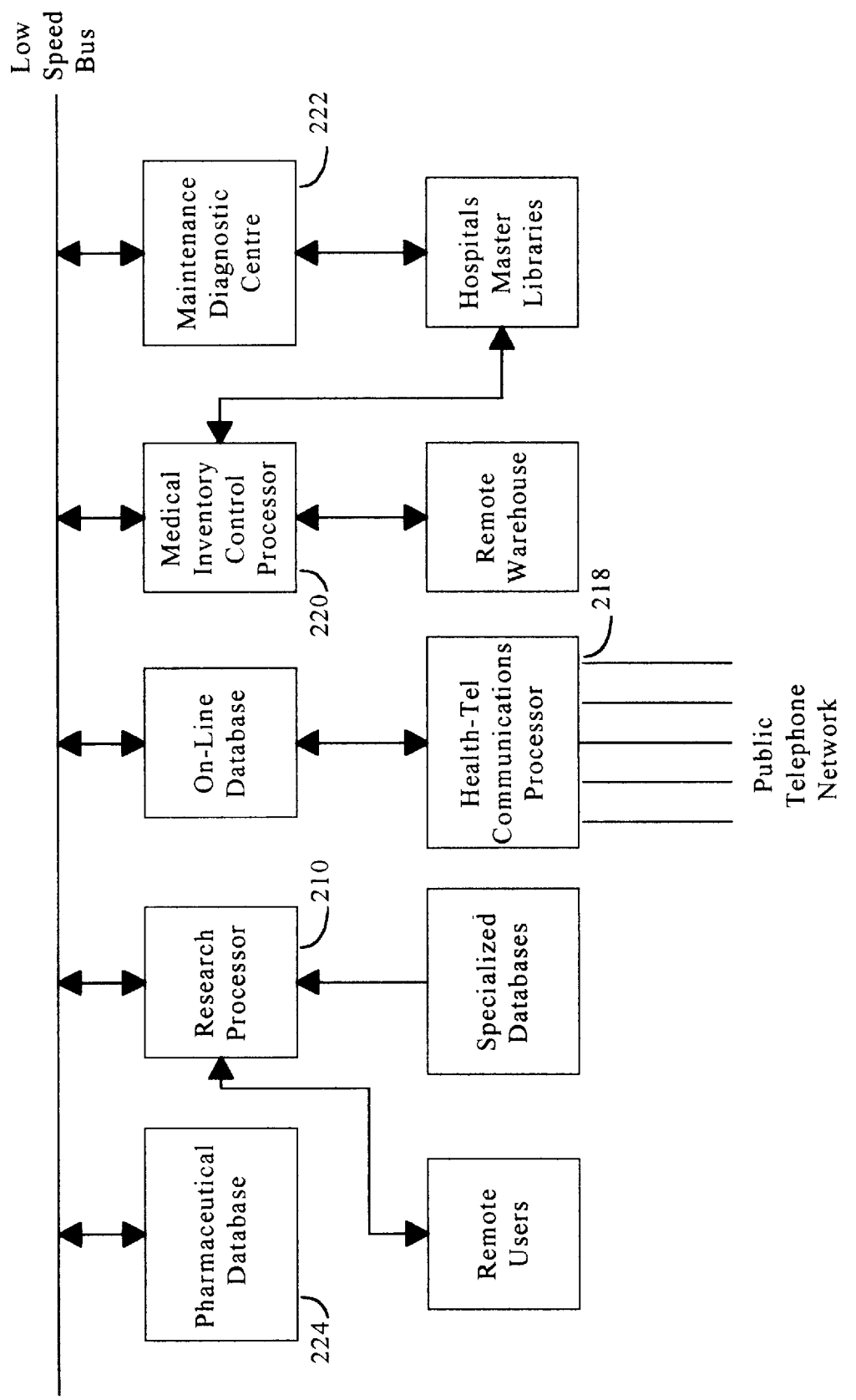

Remote from the hospital sites, a regional medical library is to be established. These are large data storage complexes (202) based around a large computer system (Cambridge, Convex, IBM, etc.) and mass memory storage (204) (Storage Technology, Ampex, EMASS, or Metrum Peripheral Products). Refer to FIG. 7A and 7B. This regional library is capable of providing compression services (video compression systems (206) are available from IBM, DEC, SGI, etc.) to suitable quality levels determined by the application i.e. movie video distribution, educational videos, medical training packages with high resolution medical images, etc. As a result, the regional library contains several compression services in software and hardware forms (C-Cube, Optibase, XING, Apple, etc.) and thus can take advantage of the latest development in compression technology. Compression capabilities for textual and graphical data also reside in this regional library. These compressed products are then distributed via video servers (226) and high speed memory buffers (228) back to the hospitals' master libraries, to third party users such as medical training universities, to clinics/laboratories, physician offices (208), and even to patient's residences if necessary. This distribution is via DBS, fiber optics, coaxial cable, wireless means, or twisted pair telephone cabling depending on the communications capability at the user facility and the amount of data and the required bandwidth necessary to implement distribution.

This regional library also has the capability to allocate dedicated services to specialized medical research fields (210) i.e. cancer, diabetes, altziemers, etc. This is accomplished by acquiring all the relevant information on the specific field from all the interconnected hospital master libraries. Applicable confidential patient identification has been purged from this data, leaving only the relevant medical data. A similar software management and data search/sort (Fulcrum's SearchTools) capability as described for the hospital master libraries is available to satisfy requests by research oriented users. Each user pays a per use access fee for usage of these research oriented databases.

This regional library also acts as a distribution hub for the dissemination of new medical information or electronic medical literature in compressed format. This is especially relevant to large hospital organizations that require the dissemination of information to all their member hospitals. For instance, new information relating to new drug types (224) and their use and application is easily distributed automatically to interested parties i.e. users have been screened into specialized categories such as cancer related issues. These authorized users include registered hospitals, medical clinics, and the offices of general practitioners with the distribution of this data via DBS, fiber optics, coaxial cable, or telephone cabling (212). Typical data such as this likely contain images, so the data is compressed to permit the distribution of video images and to minimize the communication link charges. Other typical types of information include data pertaining to new prothesis components, literature relating to new/changes to medical coverage insurance plans, changes to legal/governmental medical policy, etc. The regional library becomes a centre for the dissemination of all medical related information. This encourages the expansion and use of the overall medical network system.

The regional library contains software authoring tools (Video for Windows*, Actionmedia II*, Indeo*, Adobe*, Quicktime*, etc.) to allow the production of medical educational and training materials. Hardware to generate CD-ROM masters (214) to assist in the distribution of this training material is also available. This is extremely important with respect to the association between the regional library, the offices of the general practitioners, medical clinics, lobbies of hospitals, and other medical facilities. A medical diagnostic node (information kiosk) (216) is to be established at each location consisting of a PC, a monitor, and a CD-ROM player. Through an interactive menu, an interested user scans through a database to conduct a preliminary self diagnosis, obtain information on specific drugs, their application and any potential effects, nutrition and dietary data, etc. The intent is to make the user more informed as to their own medical problems and related health care. To complement this capability, a phone in line known as HealthTel (218), is staffed by expert medical personnel to assist in further diagnosis or for the general dissemination of medical information.

In association with the regional library (not necessarily at the same location) is a centralized warehouse for the distribution of all medical supplies or consumables. This warehouse (220) is linked with the hospitals' master libraries or an organization's overall inventory control system to automatically order, distribute, and invoice for the requested medical merchandise. This is effected through the use of standard Electronic Data Interchange (EDI) file formats for order forms, invoices, etc.

The regional library also contains a maintenance diagnostic centre (222). From this facility a maintenance technician is capable of accessing any hospital master library and indirectly any PCS unit, and invoke the running of maintenance diagnostics. Thus from a remote facility, equipment servicing is accomplished to assist local maintenance personnel in the diagnosis of equipment failures.

Thus it is apparent that there has been provided in accordance with the invention that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What we claim as our invention:

1. An electronic information system for distribution of medical information and patient services comprising:

(a) a data source in the form of a Master Library (ML) storing data in digital compressed format, the ML being adapted to store unprocessed or digitally compressed data selected from one or more of the following:
  (i) patient/medical staff health record information,
  (ii) clinical data including X-Ray, MRI and video images,
  (iii) patient laboratory data to support medical diagnoses and investigations,
  (iv) educational/training information in video or textual format for the training of medical personnel and patient requirements,
  (v) pharmaceutical databases,
  (vi) entertainment audio/video data,
  (vii) monitored video of critical areas including operating rooms and psychiatric wards,
  (viii) general security video monitoring data, and
  (ix) management information data including accounting/billing and inventory control/ordering services;
(b) a communications interconnection system electronically associated with the ML;
(c) a computerized nursing station electronically associated with the ML through the internal medical information network for temporary storage of patients' health records that have been accessed and downloaded from the ML, said nursing station operating as a client/server computer system, wherein the server computer is part of the nursing station and the client systems are the interconnected Patient Care Stations (PCS). The nursing station server system containing disk and random access memory (RAM) and the server computer to temporarily store health records for patients interfaced to this station;
(d) an electronic PCS comprising client computers located at each patient bedside communicating with the nursing station server system, said client computers each comprising a central processing unit with associated memory and the following items:
  (i) a monitor screen for display of normal NTSC video, RGB video and other interfaced/non-interlaced digital video formats;
  (ii) interface means to electronically communicate through the communications interconnection system with the ML and with the nursing station;
  (iii) a wireless/IR transmitter/receiver to communicate with a pen based computer device (Personal Data Assistant or PDA);
  (iv) an input entry device to facilitate the patient/medical staff communication within the system;
  (v) compression and decompression means for data passed to and from the patient care station; and
  (vi) application software supplying patient and medical staff services.

2. A system according to claim 1 wherein the computerized nursing station is further provided with decompression means to process any data received from the ML and compression means for processing any data to be transmitted to the ML.

3. A system according to claim 1 wherein the monitor is a unit selected from the group comprising a cathode ray tube, and computer display panels.

4. A system according to claim 1 wherein the communications interconnection system is provided with a cable switched voice means to interface between the patient and a public telephone network.

5. A system according to claim 1 provided with data storage, search, and retrieval implemented through an interactive software means allowing the user to search the ML databases and retrieve data based on user defined search criteria.

6. A system according to claim 1 that incorporates around the ML a unique security architecture.

7. A system according to claim 1 that incorporates an unique security architecture around the PCS and PDA.

8. A system according to claim 1 that contains a secure user's signature pen (utilized in association with the PDA) that contains a digitized compressed data replica of the user's signature to be used to verify that the user is an authorized user of the system.

9. A system according to claim 1 that has been programmed to audit user access to all the archived electronic health records contained in the ML.

10. A system according to claim 1 wherein the data is passed to and from the master library by means selected from the group comprising DBS, fiber optic, twisted pair, co-axial cable or wireless communication.

11. A system according to claim 1 wherein the master library is provided with means to receive and store, in digitally compressed form, data from one or more of the following:
    (a) physicians offices;
    (b) clinics and laboratories;
    (c) video entertainment libraries;
    (d) electronic medical libraries;
    (e) hospital security, patient and operating room monitoring information
    (f) patient's residences.

12. A system according to claim 11 further comprising one or more decompression means associated with the master library to provide access to the information stored therein by suitably decompressing the compressed data for viewing.

13. A system according to claim 1 wherein the patient care station is further provided with internal memory means for storage of data in digitally compressed form that has been downloaded from either the nursing station server system or the ML.

14. A system according to claim 13 wherein the client computer of the patient care station is programmed to provide an interactive menu for the selection of services comprising:
    (a) meal selection,
    (b) selection of electronic entertainment and information packages selected from the group comprising regular TV programming, movie videos on demand, video games, educational information, clinical data and administrative data;
    (c) and third party oriented services selected from the group comprising florist, giftshop, chaplain, physiotherapist.

15. A system according to claim 1 wherein the patient care station is further interfaced with an external pen based computer or PDA which has the integral electronic means for reading smart health card patient information and for documenting medical diagnosis results.

16. A system according to claim 15 wherein the integral electronic means is a Personal Computer Memory Card International Association (PCMCIA) smart card reader/writer.

17. A system according to claim 1 comprising a plurality of nursing stations, with one or more patient care stations being electronically associated with each said nursing station.

18. A system according to claim 17 wherein each patient care station is provided with a unique addressable identification code ensuring a one to one correspondence between a patient's bed location and the master library which manages these codes.

19. A system according to claim 18 wherein the PCS incorporates a Personal Computer Memory Card International Association (PCMCIA) reader/writer(s) pluggable module to receive, read and write a smart health card unique to the corresponding patient, and to facilitate optional features such as extra memory, FAX/modems, special LAN interfaces, and user personality cards.

* * * * *